(12) United States Patent
Kaye et al.

(10) Patent No.: US 11,514,137 B1
(45) Date of Patent: Nov. 29, 2022

(54) ALTERNATIVE THERAPY IDENTIFICATION SYSTEM

(71) Applicant: McKesson Corporation, Irving, TX (US)

(72) Inventors: Elizabeth S. Kaye, Suwanee, GA (US); Stacy Hopkins, Loganville, GA (US)

(73) Assignee: MCKESSON CORPORATION, Irving, TX (US)

( * ) Notice: Subject to any disclaimer, the term of this patent is extended or adjusted under 35 U.S.C. 154(b) by 229 days.

(21) Appl. No.: 15/085,166

(22) Filed: Mar. 30, 2016

(51) Int. Cl.
*G16H 50/30* (2018.01)
*G06F 19/00* (2018.01)

(52) U.S. Cl.
CPC .......... *G06F 19/328* (2013.01); *G06F 19/325* (2013.01); *G06F 19/3456* (2013.01)

(58) Field of Classification Search
CPC ... G06F 19/328; G06F 19/325; G06F 19/3456
See application file for complete search history.

(56) References Cited

U.S. PATENT DOCUMENTS

| | | |
|---|---|---|
| 5,012,035 A | 4/1991 | Sartori et al. |
| 5,173,851 A | 12/1992 | Off et al. |
| 5,595,342 A | 1/1997 | McNair et al. |
| 5,628,530 A | 5/1997 | Thornton |
| 5,726,092 A | 3/1998 | Mathews et al. |
| 5,757,898 A | 5/1998 | Nishikawa |
| 5,769,228 A | 6/1998 | Wroblewski |
| 6,012,035 A | 1/2000 | Freeman et al. |
| 6,111,218 A | 8/2000 | Akers et al. |
| 6,463,462 B1 | 10/2002 | Smith et al. |
| 6,595,342 B1 | 7/2003 | Maritzen et al. |
| 6,726,092 B2 | 4/2004 | Goldberg et al. |
| 6,757,898 B1 | 6/2004 | Ilsen et al. |
| 6,769,228 B1 | 8/2004 | Mahar |
| 7,155,397 B2 | 12/2006 | Alexander et al. |
| 7,192,741 B2 | 3/2007 | Otte et al. |
| 7,337,129 B1 | 2/2008 | Lowry et al. |
| 7,346,768 B2 | 3/2008 | DiRienzo |
| 7,409,632 B1 | 8/2008 | DiRienzo |

(Continued)

FOREIGN PATENT DOCUMENTS

| | | |
|---|---|---|
| AU | 2003243327 A | 12/2003 |
| CA | 2 482 370 A1 | 3/2006 |

(Continued)

OTHER PUBLICATIONS

Almaro, Moshe; "Recovery and Reuse of Unused Prescription Drugs" MIT What Matters: Aug. 2005.

(Continued)

*Primary Examiner* — Michael Tomaszewski
*Assistant Examiner* — Mohmad Muqueeth
(74) *Attorney, Agent, or Firm* — Alston & Bird LLP

(57) ABSTRACT

An improved alternative therapy identification system increases the efficiency for obtaining information for alternative therapies. The alternative therapy identification system automates alternative therapy identification information from both a product level and a drug cost level. The improved alternative therapy identification system may also increase the efficiency by improving alternative therapy selection to occur at the prescriber level.

18 Claims, 10 Drawing Sheets

(56) References Cited

U.S. PATENT DOCUMENTS

| | | | |
|---|---|---|---|
| 7,734,483 B1 * | 6/2010 | Smith | G06F 19/328 |
| | | | 705/3 |
| 7,783,383 B2 | 8/2010 | Eliuk et al. | |
| 7,840,424 B2 | 11/2010 | Wiley et al. | |
| 7,856,364 B1 | 12/2010 | Wiley et al. | |
| 7,912,741 B1 * | 3/2011 | Pinsonneault | G06Q 10/10 |
| | | | 600/300 |
| 7,921,021 B1 | 4/2011 | Newman | |
| 8,036,913 B1 | 10/2011 | Pinsonneault et al. | |
| 8,036,914 B1 | 10/2011 | Pinsonneault | |
| 8,036,918 B1 | 10/2011 | Pinsonneault | |
| 8,050,943 B1 | 11/2011 | Wiley et al. | |
| 8,060,379 B1 * | 11/2011 | Pinsonneault | G06Q 30/06 |
| | | | 705/2 |
| 8,326,773 B1 | 12/2012 | Bellamy | |
| 8,412,537 B1 | 4/2013 | Fenton et al. | |
| 8,489,415 B1 * | 7/2013 | Ringold | G06Q 10/10 |
| | | | 705/2 |
| 8,521,557 B1 | 8/2013 | Ringold et al. | |
| 8,560,340 B1 | 10/2013 | Ringold | |
| 8,645,162 B2 | 2/2014 | Boerger et al. | |
| 8,671,018 B2 | 3/2014 | Thomas et al. | |
| 8,738,399 B1 | 5/2014 | Abou Nader et al. | |
| 8,786,650 B1 | 7/2014 | Eller et al. | |
| 8,984,059 B2 | 3/2015 | Johnson | |
| 9,026,507 B2 | 5/2015 | Shraim et al. | |
| 9,100,793 B2 | 8/2015 | Johnson | |
| 9,171,322 B2 | 10/2015 | Spievak et al. | |
| 9,356,947 B2 | 5/2016 | Shraim et al. | |
| 9,760,871 B1 | 9/2017 | Pourfallah et al. | |
| 10,157,262 B1 | 12/2018 | Pinsonneault | |
| 10,417,380 B1 | 9/2019 | Kaye et al. | |
| 10,489,552 B2 | 11/2019 | Pinsonneault | |
| 10,496,793 B1 | 12/2019 | Lawrence et al. | |
| 10,565,656 B1 | 2/2020 | Pinsonneault et al. | |
| 10,606,984 B1 | 3/2020 | Kaye et al. | |
| 10,616,146 B1 | 4/2020 | Hopkins et al. | |
| 10,628,797 B2 | 4/2020 | Shraim et al. | |
| 10,642,812 B1 | 5/2020 | Hopkins et al. | |
| 10,713,694 B1 | 7/2020 | Harris et al. | |
| 10,747,848 B2 | 8/2020 | Guinan | |
| 10,778,618 B2 | 9/2020 | Karnin et al. | |
| 10,862,832 B1 | 12/2020 | Harris | |
| 10,924,545 B2 | 2/2021 | Momchilov et al. | |
| 10,924,585 B1 | 2/2021 | Harris et al. | |
| 10,929,932 B1 | 2/2021 | Golden et al. | |
| 10,978,198 B1 | 4/2021 | Pinsonneault | |
| 10,999,224 B1 | 5/2021 | Frechen et al. | |
| 2001/0027403 A1 | 10/2001 | Peterson et al. | |
| 2001/0029483 A1 | 10/2001 | Schultz et al. | |
| 2001/0037216 A1 | 11/2001 | Oscar et al. | |
| 2001/0039589 A1 | 11/2001 | Aho et al. | |
| 2001/0056359 A1 | 12/2001 | Abreu | |
| 2002/0002495 A1 | 1/2002 | Ullman | |
| 2002/0004812 A1 | 1/2002 | Motoyama | |
| 2002/0032582 A1 | 3/2002 | Feeney et al. | |
| 2002/0032583 A1 | 3/2002 | Joao | |
| 2002/0035484 A1 | 3/2002 | McCormick | |
| 2002/0087583 A1 | 7/2002 | Morgan et al. | |
| 2002/0111832 A1 | 8/2002 | Judge | |
| 2002/0147614 A1 | 10/2002 | Doerr et al. | |
| 2002/0198831 A1 | 12/2002 | Patricelli et al. | |
| 2003/0009367 A1 | 1/2003 | Morrison | |
| 2003/0050796 A1 | 3/2003 | Baldwin | |
| 2003/0050799 A1 | 3/2003 | Jay et al. | |
| 2003/0069760 A1 | 4/2003 | Gelber | |
| 2003/0074234 A1 | 4/2003 | Stasny | |
| 2003/0097310 A1 | 5/2003 | Ono et al. | |
| 2003/0149625 A1 | 8/2003 | Leonardi et al. | |
| 2003/0154163 A1 | 8/2003 | Phillips et al. | |
| 2003/0172008 A1 | 9/2003 | Hage et al. | |
| 2003/0187690 A1 | 10/2003 | Miller | |
| 2003/0229540 A1 | 12/2003 | Algiene | |
| 2003/0236747 A1 | 12/2003 | Sager | |
| 2004/0039599 A1 | 2/2004 | Fralic | |
| 2004/0054685 A1 | 3/2004 | Rahn et al. | |
| 2004/0059607 A1 | 3/2004 | Ball et al. | |
| 2004/0073456 A1 | 4/2004 | Gottlieb et al. | |
| 2004/0073457 A1 | 4/2004 | Kalies | |
| 2004/0078222 A1 | 4/2004 | Khan et al. | |
| 2004/0078234 A1 | 4/2004 | Tallal, Jr. | |
| 2004/0088187 A1 | 5/2004 | Chudy et al. | |
| 2004/0103062 A1 | 5/2004 | Wood et al. | |
| 2004/0117323 A1 | 6/2004 | Mindala | |
| 2004/0148198 A1 | 7/2004 | Kalies | |
| 2004/0153336 A1 | 8/2004 | Virdee et al. | |
| 2004/0199545 A1 | 10/2004 | Wagner et al. | |
| 2004/0236630 A1 | 11/2004 | Kost et al. | |
| 2004/0249745 A1 | 12/2004 | Baaren | |
| 2005/0015280 A1 | 1/2005 | Gabel et al. | |
| 2005/0060201 A1 | 3/2005 | Connely, III et al. | |
| 2005/0075932 A1 | 4/2005 | Mankoff | |
| 2005/0080692 A1 | 4/2005 | Padam et al. | |
| 2005/0102169 A1 | 5/2005 | Wilson | |
| 2005/0154627 A1 | 7/2005 | Zuzek et al. | |
| 2005/0187793 A1 | 8/2005 | Myles | |
| 2005/0197862 A1 | 9/2005 | Paterson et al. | |
| 2005/0240442 A1 | 10/2005 | Lapsker et al. | |
| 2005/0240473 A1 | 10/2005 | Ayers, Jr. et al. | |
| 2005/0261939 A1 | 11/2005 | Augspurger et al. | |
| 2005/0288972 A1 | 12/2005 | Marvin et al. | |
| 2006/0020514 A1 | 1/2006 | Yered | |
| 2006/0026041 A1 | 2/2006 | Ullman | |
| 2006/0036470 A1 | 2/2006 | Oaks | |
| 2006/0085231 A1 | 4/2006 | Brofman | |
| 2006/0085385 A1 | 4/2006 | Foster et al. | |
| 2006/0113376 A1 | 6/2006 | Reed et al. | |
| 2006/0149595 A1 | 7/2006 | Williams et al. | |
| 2006/0149784 A1 | 7/2006 | Tholl et al. | |
| 2006/0184391 A1 | 8/2006 | Barre et al. | |
| 2006/0212318 A1 | 9/2006 | Dooley | |
| 2006/0212345 A1 | 9/2006 | Soza et al. | |
| 2006/0224414 A1 | 10/2006 | Astrup et al. | |
| 2006/0224417 A1 | 10/2006 | Werner | |
| 2006/0224443 A1 | 10/2006 | Soza et al. | |
| 2006/0235747 A1 | 10/2006 | Hammond et al. | |
| 2006/0259363 A1 | 11/2006 | Jhetam et al. | |
| 2007/0005402 A1 | 1/2007 | Kennedy et al. | |
| 2007/0033137 A1 | 2/2007 | Provost et al. | |
| 2007/0043589 A1 | 2/2007 | Warren et al. | |
| 2007/0043595 A1 | 2/2007 | Pederson | |
| 2007/0050209 A1 | 3/2007 | Yered | |
| 2007/0050210 A1 | 3/2007 | Wiley, II | |
| 2007/0067186 A1 * | 3/2007 | Brenner | G06Q 50/22 |
| | | | 705/2 |
| 2007/0094133 A1 | 4/2007 | Anandarao et al. | |
| 2007/0108053 A1 | 5/2007 | Cramer et al. | |
| 2007/0136100 A1 | 6/2007 | Daugherty et al. | |
| 2007/0162303 A1 | 7/2007 | Wiley et al. | |
| 2007/0185799 A1 | 8/2007 | Harrison et al. | |
| 2007/0191985 A1 | 8/2007 | Bain | |
| 2007/0194352 A1 | 8/2007 | Han | |
| 2007/0202886 A1 | 8/2007 | Dhebri et al. | |
| 2007/0204043 A1 | 8/2007 | Espinosa et al. | |
| 2007/0219813 A1 | 9/2007 | Moore | |
| 2007/0233525 A1 | 10/2007 | Boyle | |
| 2007/0233526 A1 | 10/2007 | Hoffman et al. | |
| 2007/0239493 A1 | 10/2007 | Sweetland et al. | |
| 2007/0250341 A1 | 10/2007 | Howe et al. | |
| 2007/0260750 A1 | 11/2007 | Feied et al. | |
| 2007/0276697 A1 | 11/2007 | Wiley et al. | |
| 2007/0294765 A1 | 12/2007 | Rihn et al. | |
| 2007/0299915 A1 | 12/2007 | Shraim et al. | |
| 2008/0033750 A1 | 2/2008 | Swiss et al. | |
| 2008/0103836 A1 | 5/2008 | Park et al. | |
| 2008/0112411 A1 | 5/2008 | Stafford et al. | |
| 2008/0152107 A1 | 6/2008 | Mendiola | |
| 2008/0215361 A1 | 9/2008 | Nunnari et al. | |
| 2008/0262948 A1 | 10/2008 | Grady et al. | |
| 2009/0030719 A1 | 1/2009 | Nadas et al. | |
| 2009/0064330 A1 | 3/2009 | Shraim et al. | |
| 2009/0094051 A1 * | 4/2009 | Ard | G06Q 30/06 |
| | | | 705/2 |
| 2009/0100099 A1 | 4/2009 | Buckwaiter | |

(56) References Cited

U.S. PATENT DOCUMENTS

| | | |
|---|---|---|
| 2009/0112707 A1 | 4/2009 | Weiss et al. |
| 2009/0204477 A1 | 8/2009 | Urso |
| 2009/0287558 A1 | 11/2009 | Seth et al. |
| 2009/0313112 A1 | 12/2009 | Champ et al. |
| 2009/0327363 A1 | 12/2009 | Cullen et al. |
| 2010/0030667 A1 | 2/2010 | Chudy et al. |
| 2010/0070298 A1 | 3/2010 | Kalies |
| 2010/0144259 A1 | 6/2010 | Allexon et al. |
| 2010/0145730 A1 | 6/2010 | Abreu |
| 2010/0161353 A1 | 6/2010 | Mayaud |
| 2010/0217622 A1 | 8/2010 | Brown et al. |
| 2010/0285821 A1 | 11/2010 | Smeeding et al. |
| 2010/0293236 A1 | 11/2010 | Wisner et al. |
| 2011/0112871 A1 | 5/2011 | Simonowski et al. |
| 2011/0161109 A1 | 6/2011 | Pinsonneault et al. |
| 2011/0196697 A1 | 8/2011 | Akers |
| 2011/0288925 A1 | 11/2011 | Thomas et al. |
| 2012/0053958 A1 | 3/2012 | Marshall et al. |
| 2012/0136809 A1 | 5/2012 | Cannata et al. |
| 2012/0143627 A1 | 6/2012 | Ruben et al. |
| 2012/0166268 A1 | 6/2012 | Griffiths |
| 2012/0179481 A1 | 7/2012 | Patel et al. |
| 2012/0185263 A1 | 7/2012 | Emert |
| 2012/0185264 A1 | 7/2012 | Demogenes et al. |
| 2012/0253829 A1 | 10/2012 | John et al. |
| 2012/0253830 A1 | 10/2012 | John et al. |
| 2012/0253831 A1 | 10/2012 | John et al. |
| 2012/0253832 A1 | 10/2012 | John et al. |
| 2012/0253833 A1 | 10/2012 | John et al. |
| 2012/0253846 A1 | 10/2012 | John et al. |
| 2012/0265591 A1 | 10/2012 | Hwang |
| 2013/0041968 A1 | 2/2013 | Cohen et al. |
| 2013/0103602 A1 | 4/2013 | Melnick et al. |
| 2013/0144715 A1 | 6/2013 | Kranzley et al. |
| 2013/0197980 A1 | 8/2013 | Lerner et al. |
| 2013/0246082 A1 | 9/2013 | Brylawski et al. |
| 2013/0311389 A1 | 11/2013 | Kaehler et al. |
| 2014/0039911 A1 | 2/2014 | Iyer |
| 2014/0088985 A1 | 3/2014 | Grant et al. |
| 2014/0214435 A1 | 7/2014 | Previdi |
| 2014/0249861 A1 | 9/2014 | Gamble et al. |
| 2014/0249864 A1 | 9/2014 | Sultan et al. |
| 2014/0278456 A1 | 9/2014 | Milosevich et al. |
| 2015/0088557 A1 | 3/2015 | Huynh et al. |
| 2015/0142479 A1 | 5/2015 | Porter et al. |
| 2015/0149197 A1 | 5/2015 | Guinan |
| 2015/0154565 A1 | 6/2015 | Kaehler et al. |
| 2015/0154588 A1 | 6/2015 | Purves et al. |
| 2015/0195224 A1 | 7/2015 | Karnin et al. |
| 2015/0213195 A1 | 7/2015 | Blechman |
| 2015/0234991 A1 | 8/2015 | Pinsonneault |
| 2015/0235177 A1 | 8/2015 | Shraim et al. |
| 2015/0269695 A1 | 9/2015 | Pinsonneault et al. |
| 2015/0332422 A1 | 11/2015 | Gilmartin |
| 2015/0371000 A1 | 12/2015 | Pinsonneault |
| 2016/0012465 A1 | 1/2016 | Sharp |
| 2016/0140593 A1 | 5/2016 | Smeeding et al. |
| 2016/0213512 A1 | 7/2016 | Palanker et al. |
| 2016/0267544 A1 | 9/2016 | Flood et al. |
| 2016/0267545 A1 | 9/2016 | Glass et al. |
| 2016/0307195 A1 | 10/2016 | Cantwell et al. |
| 2016/0358142 A1 | 12/2016 | Hillen |
| 2016/0359795 A1 | 12/2016 | Fehling |
| 2017/0034087 A1 | 2/2017 | Borenstein et al. |
| 2017/0220768 A1 | 8/2017 | Tanner, Jr. et al. |
| 2017/0323295 A1 | 11/2017 | Kranzley et al. |
| 2017/0324695 A1 | 11/2017 | Fischer et al. |
| 2018/0012244 A1 | 1/2018 | Leonardi |
| 2018/0366810 A1 | 12/2018 | Nero et al. |
| 2019/0213212 A1 | 7/2019 | Adato et al. |
| 2019/0385733 A1 | 12/2019 | Kaye et al. |
| 2019/0385734 A1 | 12/2019 | Pinsonneault |
| 2021/0319887 A1 | 10/2021 | Derrick, Jr. et al. |

FOREIGN PATENT DOCUMENTS

| | | |
|---|---|---|
| CA | 2792252 A1 | 4/2013 |
| CA | 2810686 A1 | 10/2013 |
| CN | 102362778 | 2/2012 |
| KR | 100755440 | 9/2007 |
| KR | 100793852 | 1/2008 |
| KR | 101038074 | 6/2011 |
| KR | 101101692 | 12/2011 |
| KR | 20110138108 | 12/2011 |
| KR | 20110138572 | 12/2011 |
| KR | 101154858 | 6/2012 |
| WO | WO 1991/006917 | 5/1991 |
| WO | WO 1995/003569 A2 | 2/1995 |
| WO | WO 1997/025682 | 7/1997 |
| WO | WO 1998/050871 | 11/1998 |
| WO | WO 2000/039737 A1 | 7/2000 |
| WO | WO 3098401 | 11/2003 |
| WO | WO 2007/025295 A2 | 3/2007 |
| WO | WO 2007/094772 A1 | 8/2007 |
| WO | WO 2008/092109 | 7/2008 |

OTHER PUBLICATIONS

American Society of Health-System Pharmacists (ASHP), "Is Prescribing the Next Step in the Evolution of Pharmacy?" May 15, 2012.

Anonymous, ACS to Demonstrate Electronic Health Record Solution Suite at MMIS 2007 Conference; EHR Tools Consolidate Data, Provide Useful Information at the Point of Care for Medicaid Providers, Payers, and Patients, PR Newswire, Aug. 13, 2007, New York, NY, USA.

Anonymous, Medic; On-line Goes In-House, Chain Store Age Executive, Jan. 1987, vol. 63, Issue 1, USA; Abstract only.

Anonymous, Pharmacy Industry Leaders Launch Firm to Supply Real-Time Data, PR Newswire, Jul. 30, 2001, p. 1, New York, NY, USA.

Anonymous, TechRx Announces Successful Beta Deployment of T-Rex. PR Newswire. May 13, 2002.

Consalvo, Bob; "City of Bosont in the City Council" hearing notice, Dec. 6, 2006.

Coping with Information Overload. The News Source for Healthcare Information Technology [Online] Nov. 2004. URL: http://www.awarix.com.

Final Office Action for U.S. Appl. No. 12/140,015 dated Jan. 31, 2011.

Final Office Action for U.S. Appl. No. 12/415,062 dated Oct. 6, 2011.

Final Office Action for U.S. Appl. No. 12/555,589 dated Apr. 11, 2012.

Final Office Action for U.S. Appl. No. 12/560,071 dated Aug. 28, 2015.

Final Office Action for U.S. Appl. No. 12/560,071 dated Nov. 8, 2012.

Final Office Action for U.S. Appl. No. 12/570,982 dated Apr. 11, 2014.

Final Office Action for U.S. Appl. No. 12/570,982 dated Aug. 28, 2015.

Final Office Action for U.S. Appl. No. 12/570,982 dated Jan. 17, 2013.

Final Office Action for U.S. Appl. No. 12/730,015 dated Aug. 14, 2012.

Final Office Action for U.S. Appl. No. 12/978,898 dated May 16, 2013.

Final Office Action for U.S. Appl. No. 13/721,890 dated Jun. 24, 2015.

Final Office Action for U.S. Appl. No. 13/721,890 dated Nov. 25, 2016.

Final Office Action for U.S. Appl. No. 13/782,909 dated May 31, 2016.

Final Office Action for U.S. Appl. No. 13/782,909 dated Oct. 6, 2015.

Final Office Action for U.S. Appl. No. 13/804,175 dated Oct. 6, 2015.

(56) References Cited

OTHER PUBLICATIONS

Final Office Action for U.S. Appl. No. 14/090,113 dated Jan. 6, 2016.
Final Office Action for U.S. Appl. No. 14/090,122 dated Apr. 22, 2016.
Final Office Action for U.S. Appl. No. 14/193,294 dated May 2, 2016.
Final Office Action for U.S. Appl. No. 14/218,326 dated Jun. 30, 2016.
Kaplan et al., "Let the Needles Do the Talking! Evaluating the New Haven Needle Exchange." Interfaces 23:1, Jan.-Feb. 1993 (pp. 7-26).
Lamb, J., New Era of Electronic Medicine Management: E-Prescriptions, Britain's Traditionally Cautious National Health Service is Starting Trials for Online Prescription, with the Aim of Cutting Costs, Finance Times, London, Feb. 21, 2001, p. 6, London, United Kingdom.
Letter Restarting Period for Response for U.S. Appl. No. 13/721,890 dated Jan. 14, 2015.
Marie Chisholm et al. "Pharmaceutical Manufacturer Assistance Program." Arch Intern Med. vol. 162, Apr. 8, 2002.
Non-Anal Office Action for U.S. Appl. No. 13/721,890 dated Jun. 14, 2016.
Non-Final Office Action for U.S. Appl. No. 12/560,071 dated Jun. 21, 2012.
Non-Final Office Action for U.S. Appl. No. 12/570,982 dated Jun. 20, 2012.
Non-Final Office Action for U.S. Appl. No. 14/193,294 dated Feb. 21, 2017.
Non-final Office Action for U.S. Appl. No. 12/140,015 dated Oct. 8, 2010.
Non-final Office Action for U.S. Appl. No. 12/189,650 dated Jan. 22, 2010.
Non-final Office Action for U.S. Appl. No. 12/189,654 dated Jan. 22, 2010.
Non-Final Office Action for U.S. Appl. No. 12/415,062 dated Mar. 30, 2011.
Non-Final Office Action for U.S. Appl. No. 12/555,589 dated Dec. 9, 2011.
Non-Final Office Action for U.S. Appl. No. 12/560,071 dated Sep. 23, 2014.
Non-Final Office Action for U.S. Appl. No. 12/570,982 dated Sep. 12, 2013.
Non-Final Office Action for U.S. Appl. No. 12/730,015 dated Mar. 6, 2012.
Non-Final Office Action for U.S. Appl. No. 12/956,411 dated Jan. 24, 2011.
Non-Final Office Action for U.S. Appl. No. 12/978,898 dated Feb. 6, 2013.
Non-Final Office Action for U.S. Appl. No. 12/982,395 dated Dec. 11, 2012.
Non-Final Office Action for U.S. Appl. No. 13/721,890 dated Jan. 9, 2015.
Non-final Office Action for U.S. Appl. No. 13/782,909 dated Feb. 11, 2016.
Notice of Allowance for U.S. Appl. No. 11/674,069 dated Jul. 19, 2010.
Notice of Allowance for U.S. Appl. No. 12/140,015 dated Jun. 10, 2011.
Notice of Allowance for U.S. Appl. No. 12/165,221 dated Nov. 16, 2010.
Notice of Allowance for U.S. Appl. No. 12/189,650 dated Aug. 13, 2010.
Notice of Allowance for U.S. Appl. No. 12/956,411 dated Aug. 5, 2011.
Notice of Allowance for U.S. Appl. No. 12/982,395 dated Apr. 24, 2013.
Office Action for U.S. Appl. No. 12/570,982 dated Apr. 8, 2015.
Office Action for U.S. Appl. No. 14/181,011 dated Feb. 29, 2016.
Office Action for U.S. Appl. No. 14/181,011 dated Mar. 20, 2017.
Office Action for U.S. Appl. No. 14/181,011 dated Oct. 20, 2016.
Office Action for U.S. Appl. No. 14/181,011 dated Sep. 12, 2017.
Office Action for U.S. Appl. No. 14/193,294 dated Aug. 4, 2017, 31 pages.
Office Action for U.S. Appl. No. 14/193,294 dated Mar. 22, 2018, 28 pages.
Office Action for U.S. Appl. No. 14/229,043 dated Jul. 24, 2017.
Office Action for U.S. Appl. No. 14/643,468 dated Mar. 8, 2018.
Office Action for U.S. Appl. No. 15/085,166 dated Jun. 29, 2018 19 pages.
Office Action for U.S. Appl. No. 13/782,909 dated Jun. 25, 2015.
Office Action for U.S. Appl. No. 13/804,175 dated Mar. 13, 2015.
Office Action for U.S. Appl. No. 14/090,122 dated Oct. 21, 2016.
Office Action for U.S. Appl. No. 14/090,122 dated Sep. 11, 2015.
Office Action for U.S. Appl. No. 14/1090,113 dated Jun. 18, 2015.
Office Action for U.S. Appl. No. 14/1218,326 dated Dec. 1, 2015.
Office Action for U.S. Appl. No. 14/193,294 dated Dec. 17, 2015.
Opar, Alisa; "Rising drug costs prompt new uses for old pills." Nature Medicine, 1211333 (2006).
Pharmacy Reject Codes NCPDP.
Sampson, R.J., Taking Control of Health Care Costs, Best's Review—Life Health Insurance Edition, Nov. 1983, vol. 84, Issue 7, USA; Abstract only.
Siller et al., "Safe Disposal of Unused Controlled Substances" Avalere Health 2008.
St. Vincent's first to use Birmingham startup's information system. The Birmingham News [Online] Apr. 11, 2005. URL: http://www.awarix.com.
St. Vincent's is Digital Flagship D. Lockridge; Birmingham Medical News [Online] Sep. 2005.
Strom, Stephanie; "Old Pills Finding New Medicine Cabinets" NY Times, May 18, 2005.
Subnotebooks,Phones, and More. St. Vincent's Gets on Track. Mobile Health Data [Online], Nov. 19, 2004. URL:http://www.awarix.com.
Two automatic identification technology, neither new in the sense if being recent developments . . . Patient Safety & Quality Healthcare [Online] Aug. 2005_ URL: http://www_awarix.com.
Wisconsin Physicians Service (WPS) Insurance Corporation, "How to Read Your Explanation of Benefits Chart," Jun. 16, 2012.
www.ncoil.org/news/DrugCards2.doc dated Apr. 2002.
Office Action for U.S. Appl. No. 14/229,043 dated Sep. 14, 2018.
Notice of Allowance for U.S. Appl. No. 14/181,011 dated May 15, 2019.
Office Action for U.S. Appl. No. 14/229,043 dated Feb. 27, 2019.
Office Acton for U.S. Appl. No. 14/229,043 dated Sep. 5, 2019.
United States Patent and Trademark Office, Notice of Allowance for U.S. Appl. No. 14/181,011, dated Feb. 13, 2019, 10 pages.
United States Patent and Trademark Office, Notice of Allowance for U.S. Appl. No. 14,643,468, dated Oct. 24, 2018, 22 pages.
Non-Final Office Action for U.S. Appl. No. 16/180,915 dated Jun. 1, 2020, 40 pages.
Notice of Allowance for U.S. Appl. No. 16/180,915 dated Dec. 11, 2020, 23 pages.
Advisory Action for U.S. Appl. No. 14/193,294 dated Nov. 9, 2017, 3 pages.
Decision to Grant European Patent Application No. 13809457.8 dated May 18, 2017.
Extended European Search Report for European Application No. 13809457.8 dated Apr. 15, 2016, 6 pages.
Notice of Allowance and Fees(s) Due for U.S. Appl. No. 15/925,011 dated Jan. 22, 2021, 15 pages.
Office Action for U.S. Appl. No. 14/193,294 dated Sep. 19, 2018, 27 pages.
Office Action for U.S. Appl. No. 15/422,184 dated Aug. 27, 2019, 16 pages.
Office Action for U.S. Appl. No. 15/422,184 dated Feb. 15, 2019, 15 pages.
Office Action for U.S. Appl. No. 15/422,184 dated Jan. 14, 2020, 19 pages.
Office Action for U.S. Appl. No. 15/422,184 dated Sep. 10, 2018, 13 pages.

(56) References Cited

OTHER PUBLICATIONS

Office Action for U.S. Appl. No. 15/925,011 dated Jun. 27, 2019, 15 pages.
Office Action for U.S. Appl. No. 15/925,011 dated Oct. 24, 2019, 19 pages.
Office Action for U.S. Appl. No. 15/925,948 dated Jun. 25, 2019, 13 pages.
Office Action for U.S. Appl. No. 15/925,948 dated Oct. 23, 2019, 18 pages.
U.S. Appl. No. 16/832,318, "Method, Apparatus, And Computer Program Product for Estimated Prescription Costs", Unpublished (Filed Mar. 27, 2020), (Stacy Hopkins, Inventor), (McKesson Corporation, Assignee), pending.
U.S. Appl. No. 17/012,565, "Method, Apparatus, and Computer Program Product for Performing an Alternative Evaluation Procedure in Response to an Electronic Message," Unpublished (filing date Sep. 4, 2020), (Stacy Hopkins, et al., Inventors) (McKesson Corporation, Assignee), pending.
U.S. Appl. No. 17/092,705, "Computing System and Method for Automatically Reversing an Action Indicated by an Electronic Message," Unpublished (filing date Nov. 9, 2020), (Patrick Harris, Inventor) (McKesson Corporation, Assignee), pending.
U.S. Appl. No. 16/792,413, "Method, Apparatus and Computer Program Product for Partitioning Prescription Transaction Costs in an Electronic Prescription Transaction," Unpublished (filed Feb. 17, 2020), (Jared Burdine, Inventor) (McKesson Corporation, Assignee), pending.
U.S. Appl. No. 16/867,286, "Method, Apparatus, and Computer Program Product for Constructing Electronic Message Responses Dependent Upon Historical Information," Unpublished (filed May 5, 2020), (Jared Burdine, et al., Inventor) (McKesson Corporation, Assignee), pending.
United States Patent and Trademark Office, Advisory Action for U.S. Appl. No. 15/422,184, dated Jun. 25, 2019, 4 pages, U.S.A.
United States Patent and Trademark Office, Advisory Action for U.S. Appl. No. 15/422,184, dated Mar. 26, 2020, 5 pages, U.S.A.
United States Patent and Trademark Office, Advisory Action for U.S. Appl. No. 15/925,011, dated Jan. 31, 2020, 3 pages, U.S.A.
United States Patent and Trademark Office, Advisory Action for U.S. Appl. No. 15/925,948, dated Jan. 31, 2020, 4 pages, U.S.A.
United States Patent and Trademark Office, Notice of Allowability received for U.S. Appl. No. 15/422,184, dated Nov. 16, 2020, 2 pages, U.S.A.
United States Patent and Trademark Office, Notice of Allowance received for U.S. Appl. No. 15/422,184, dated Oct. 13, 2020, 12 pages, U.S.A.
United States Patent and Trademark Office, Notice of Allowance received for U.S. Appl. No. 15/925,948, dated Nov. 5, 2020, 22 pages, U.S.A.
United States Patent and Trademark Office, Notice of Allowance received for U.S. Appl. No. 16/043,401, dated Aug. 10, 2020, 8 pages, U.S.A.
United States Patent and Trademark Office, Office Action for U.S. Appl. No. 15/925,011, dated Apr. 8, 2020, 17 pages, U.S.A.
United States Patent and Trademark Office, Office Action for U.S. Appl. No. 15/925,948, dated Mar. 23, 2020, 29 pages, U.S.A.
United States Patent and Trademark Office, Office Action received for U.S. Appl. No. 15/422,184, dated May 18, 2020, 31 pages, U.S.A.
United States Patent and Trademark Office, Office Action received for U.S. Appl. No. 15/925,011, dated Oct. 8, 2020, 8 pages, U.S.A.
U.S. Appl. No. 14/229,043, filed Mar. 28, 2014, Pinsonneault.
U.S. Appl. No. 15/084,034, filed Mar. 29, 2016, Geone et al.
U.S. Appl. No. 16/180,915, filed Nov. 5, 2018, Pinsonneault.
Advisory Action for U.S. Appl. No. 15/137,371 dated Feb. 25, 2019, 5 pages.
Advisory Action for U.S. Appl. No. 15/427,746 dated Jul. 2, 2019, 4 pages.
Examiner's Answer for U.S. Appl. No. 14/145,027 dated Sep. 7, 2016, 28 pages.
Final Office Action for U.S. Appl. No. 13/827,676 dated Jul. 13, 2015.
Final Office Action for U.S. Appl. No. 14/145,027 dated Nov. 19, 2015.
Final Office Action for U.S. Appl. No. 15/137,371 dated Nov. 28, 2018, 24 pages.
Final Office Action for U.S. Appl. No. 15/427,746 dated Apr. 15, 2019, 10 pages.
Non-Final Office Action for U.S. Appl. No. 12/388,956 dated Feb. 3, 2011.
Non-Final Office Action for U.S. Appl. No. 13/827,676 dated Dec. 26, 2014.
Non-final Office Action for U.S. Appl. No. 13/827,676 dated Dec. 30, 2015.
Non-Final Office Action for U.S. Appl. No. 14/145,027 dated Mar. 23, 2015.
Non-Final Office Action for U.S. Appl. No. 15/137,371 dated May 29, 2018, 33 pages.
Non-Final Office Action for U.S. Appl. No. 15/427,746 dated Oct. 18, 2018, 9 pages.
Non-Final Office Action for U.S. Appl. No. 16/819,258 dated Sep. 4, 2020, 13 pages.
Notice of Allowance for U.S. Appl. No. 12/388,956 dated Jun. 14, 2011.
Notice of Allowance for U.S. Appl. No. 15/137,371 dated May 2, 2019, 30 pages.
Notice of Allowance for U.S. Appl. No. 15/427,746 dated Dec. 4, 2019, 15 pages.
Notice of Allowance for U.S. Appl. No. 15/427,746 dated Jul. 31, 2019, 13 pages.
PTAB Decision on Appeal for U.S. Appl. No. 14/145,027 dated May 31, 2018, 12 pages.
PTAB Decision on Request for Rehearing for U.S. Appl. No. 14/145,027 dated Aug. 30, 2018, 10 pages.
Notice of Allowance received for U.S. Appl. No. 16/819,258, dated Nov. 16, 2020, 8 pages.
Non-Final Office Action received for U.S. Appl. No. 16/551,962, dated Mar. 2, 2021, 38 pages.
Supplemental Notice of Allowability received for U.S. Appl. No. 16/180,915, dated Mar. 12, 2021, 11 pages.
Non-Final Office Action received for U.S. Appl. No. 16/453,509 dated Mar. 26, 2021, 45 pages.
Non-Final Office Action received for U.S. Appl. No. 16/832,318 dated Apr. 23, 2021, 52 pages.
CMS Updates Drug Dashboards with Prescription Drug Pricing and Spending Data, Data, Medicare Part D, Prescription drugs (Mar. 14, 2019).
How to Estimate the Cost of a Prescription. Pam Olson, Sr. Client Services Executive, Navitus Health Solutions (Year: 2015).
United States Patent and Trademark Office, Final Office Action received for U.S. Appl. No. 16/453,509, dated Aug. 18, 2021, 16 pages, U.S.
United States Patent and Trademark Office, Non-Final Office Action received for U.S. Appl. No. 16/792,413, dated Aug. 5, 2021, 32 pages, U.S.
Scientific and Technical Information Center, Report of Information from Dialog (NPL (non-patent literature) Search Results, Abstracts only), dated Nov. 1, 2021, (Year: 2021), 9 pages.
United States Patent and Trademark Office, Advisory Action received for Application No. 16/453,509, dated Oct. 12, 2021, 5 pages, U.S.
United States Patent and Trademark Office, Final Office Action received for U.S. Appl. No. 16/551,962, dated Nov. 4, 2021, 32 pages, U.S.
United States Patent and Trademark Office, Final Office Action received for U.S. Appl. No. 16/832,318, dated Nov. 3, 2021, 22 pages, U.S.
United States Patent and Trademark Office, Notice of Allowance received for U.S. Appl. No. 17/092,705, dated Dec. 23, 2021, 42 pages, U.S.
United States Patent and Trademark Office, Final Office Action received for U.S. Appl. No. 16/792,413, dated Jan. 10, 2022, 80 pages, U.S.

(56) References Cited

OTHER PUBLICATIONS

United States Patent and Trademark Office, Advisory Action received for U.S. Appl. No. 16/832,318, dated Jan. 28, 2022, 4 pages, U.S.
United States Patent and Trademark Office, Non-Final Office Action received for U.S. Appl. No. 16/867,286, dated Feb. 22, 2022, 38 pages, U.S.
United States Patent and Trademark Office, Notice of Allowance received for U.S. Appl. No. 17/219,526, dated Feb. 3, 2022, 48 pages, U.S.
Zhu, V. et al., "Data for drugs available through low-cost prescription drug programs are available through pharmacy benefit manager and claims data," BMC Clinical Pharmacology, Jun. 22, 2012, vol. 12, No. 12., BioMed Central Ltd., UK.
Google NPL (non-patent literature) Search on "pharmacy payment benefit copay NDC database", retrieved from the Internet at <https://scholar.google.com/scholar?hl=en&as_sdt=3,47&g=pharmacy+payment+benefit+copay+NDC+database> on Feb. 20, 2022 at 3:02 pm, 1 page.
Google NPL (non-patent literature) Search on "pharmacy payment benefit copay NDC database", retrieved from the Internet at <https://www.google.com/search?g=pharmacy+payment+benefit+copay+ndc+database&source=int&tbs=cdr%3A1%2Ccd_min%3A1%2F1%2F2010%2 . . . > on Feb. 20, 2022 at 3:00 pm, 2 pages.
United States Patent and Trademark Office, Advisory Action received for U.S. Appl. No. 16/792,413, dated Mar. 10, 2022, 4 pages, US.
United States Patent and Trademark Office, Notice of Allowance and Fee(s) Due received for U.S. Appl. No. 17/219,526, dated Mar. 22, 2022, 11 pages, US.
United States Patent and Trademark Office, Notice of Allowance and Fee(s) Due received for U.S. Appl. No. 16/551,962, dated Mar. 16, 2022, 10 pages, US.
United States Patent and Trademark Office, Notice of Allowance and Fee(s) Due received for U.S. Appl. No. 17/092,705, dated Mar. 24, 2022, 9 pages, US.
United States Patent and Trademark Office, Notice of Allowance and Fee(s) Due received for U.S. Appl. No. 16/551,962, dated Mar. 1, 2022, 14 pages, US.
United States Patent and Trademark Office, Non-Final Office Action received for U.S. Appl. No. 17/012,565, dated Apr. 12, 2022, 19 pages, U.S.A.
United States Patent and Trademark Office, Non-Final Office Action received for U.S. Appl. No. 16/453,509, dated Apr. 28, 2022, 16 pages, U.S.A.
United States Patent and Trademark Office, Non-Final Office Action received for U.S. Appl. No. 16/552,021, dated May 3, 2022, 60 pages, U.S.A.
United States Patent and Trademark Office, Non-Final Office Action received for U.S. Appl. No. 17/175,939, dated May 12, 2022, 48 pages, U.S.A.
Chu, Kuan-Yu, et al., "Incremental analysis of the reengineering of an outpatient billing process: an empirical study in a public hospital", BMC Health Services Research, Jun. 13, 2013, vol. 13, No. 215, 8 pages, BioMed Central Ltd, UK.
Google Patents Search (including Web Search History, Prior Art Search Printable History Generator) on "pharmacy payment benefit copay NDC database) (prescription) (code) (refills) (error code) country:US before:filing:20131231", retrieved from the Internet at <https://patents.google.com/?q=pharmacy+payment+benefit+copay+NDC+database&q=prescription&q=code&q=refills&q=error+code&country=US&before=filing:20131231> retrieved on Jun. 1, 2022, 4 pages.
Google Scholar Search (including Web Search History, Prior Art Search Printable History Generator) on "pharmacy payment benefit copay NDC database prescription . . . ", retrieved from the Internet at <https://scholar.google.com/scholar?hl=en&as_sdt=0%2C47&as_ylo=2010&as_yhi=2013&q=pharmacy+payment+benefit+copay+NDC+database+pres . . . > retrieved on Jun. 1, 2022, 3 pages.
United States Patent and Trademark Office, Non-Final Office Action received for U.S. Appl. No. 16/792,413, dated May 24, 2022, 48 pages, US.
United States Patent and Trademark Office, Non-Final Office Action received for U.S. Appl. No. 17/144,426, dated May 31, 2022, 42 pages, US.
United States Patent and Trademark Office, Non-Final Office Action received for U.S. Appl. No. 16/832,318, dated Jun. 8, 2022, 17 pages, US.
United States Patent and Trademark Office, Notice of Allowance received for U.S. Appl. No. 17/092,705, dated May 31, 2022, 9 pages, US.
United States Patent and Trademark Office, Notice of Allowance received for U.S. Appl. No. 17/219,526, dated Jun. 2, 2022, 8 pages, US.
United States Patent and Trademark Office, Notice of Allowance received for U.S. Appl. No. 16/551,962, dated Jun. 8, 2022, 11 pages, US.
United States Patent and Trademark Office, Final Office Action received for U.S. Appl. No. 17/012,565, dated Jul. 25, 2022, 43 pages, U.S.
United States Patent and Trademark Office, Final Office Action received for U.S. Appl. No. 16/867,286, dated Sep. 8, 2022, 19 pages, U.S.
United States Patent and Trademark Office, Notice of Allowance received for U.S. Appl. No. 16/792,413, dated Sep. 8, 2022, 18 pages, U.S.
Dubois, Robert W., "Rx Drug Costs: List Prices Versus Net Prices And The Importance Of Staying Within The Data", Health Affairs Blog, Mar. 2019, 7 pages.
Kamal, Rabah, et al., "What are the recent and forecasted trends in prescription drug spending?" Peterson-KFF Health System Tracker, Feb. 20, 2019, 19 pages, Peterson Center on Healthcare.
Cepeda, Maria Soledad, et al., "Quantification of missing prescriptions in commercial claims databases: results of a cohort study,", Pharmacoepidemiology and Drug Safety, Apr. 2017, pp. 386-392, vol. 26, Epub Jan. 25, 2017 on Wiley Online Library.
United States Patent and Trademark Office, Notice of Allowance received for U.S. Appl. No. 17/012,565, dated Sep. 21, 2022, 11 pages, U.S.
United States Patent and Trademark Office, Notice of Allowance received for U.S. Appl. No. 16/453,509, dated Oct. 3, 2022, 23 pages, U.S.
United States Patent and Trademark Office, Final Office Action received for U.S. Appl. No. 17/175,939, dated Oct. 5, 2022, 30 pages, U.S.
United States Patent and Trademark Office, Nonfinal Office Action received for U.S. Appl. No. 17/162,461, dated Oct. 5, 2022, 47 pages, U.S.
United States Patent and Trademark Office, Nonfinal Office Action received for U.S. Appl. No. 17/158,118, dated Oct. 7, 2022, 46 pages, U.S.

* cited by examiner ion system.

ALTERNATIVE THERAPY IDENTIFICATION SYSTEM

TECHNICAL FIELD

Aspects of the disclosure relate generally to alternative therapy identification, and more particularly, to an improved alternative therapy identification system.

BACKGROUND

A healthcare provider, such as a physician, doctor's office, urgent care center, hospital (e.g., emergency room and discharge), clinical staff or the like provides numerous healthcare related products and services to patients, including providing prescription products (e.g., medications, devices, etc.). Prior to prescribing the product, a healthcare provider may check a patient's benefit information to determine whether the product the healthcare provider would like to select is product covered under the patient's benefit information as well as a corresponding patient pay amount for the selected product. However, in the event that the patient's benefits do not cover the product selected by the healthcare provider, or the patient's financial responsibility for the selected product is too costly, the healthcare provide typically does not have an option to selected an alternative drug that is equivalent to what is selected. Furthermore, the healthcare provider lacks the ability to perform a benefit inquiry that may identify an alternative product at a lower cost to the patient. As a result, the selection of alternative therapies at the prescriber level is inefficient and often costly to the patient. An improved alternative therapy identification system may reduce or eliminate certain issues related to the selection of alternative therapies for a patient.

BRIEF DESCRIPTION OF THE DRAWINGS

Reference will now be made to the accompanying drawings, which are not necessarily drawn to scale, and wherein.

DETAILED DESCRIPTION OF EXAMPLE EMBODIMENTS

Figure 1:
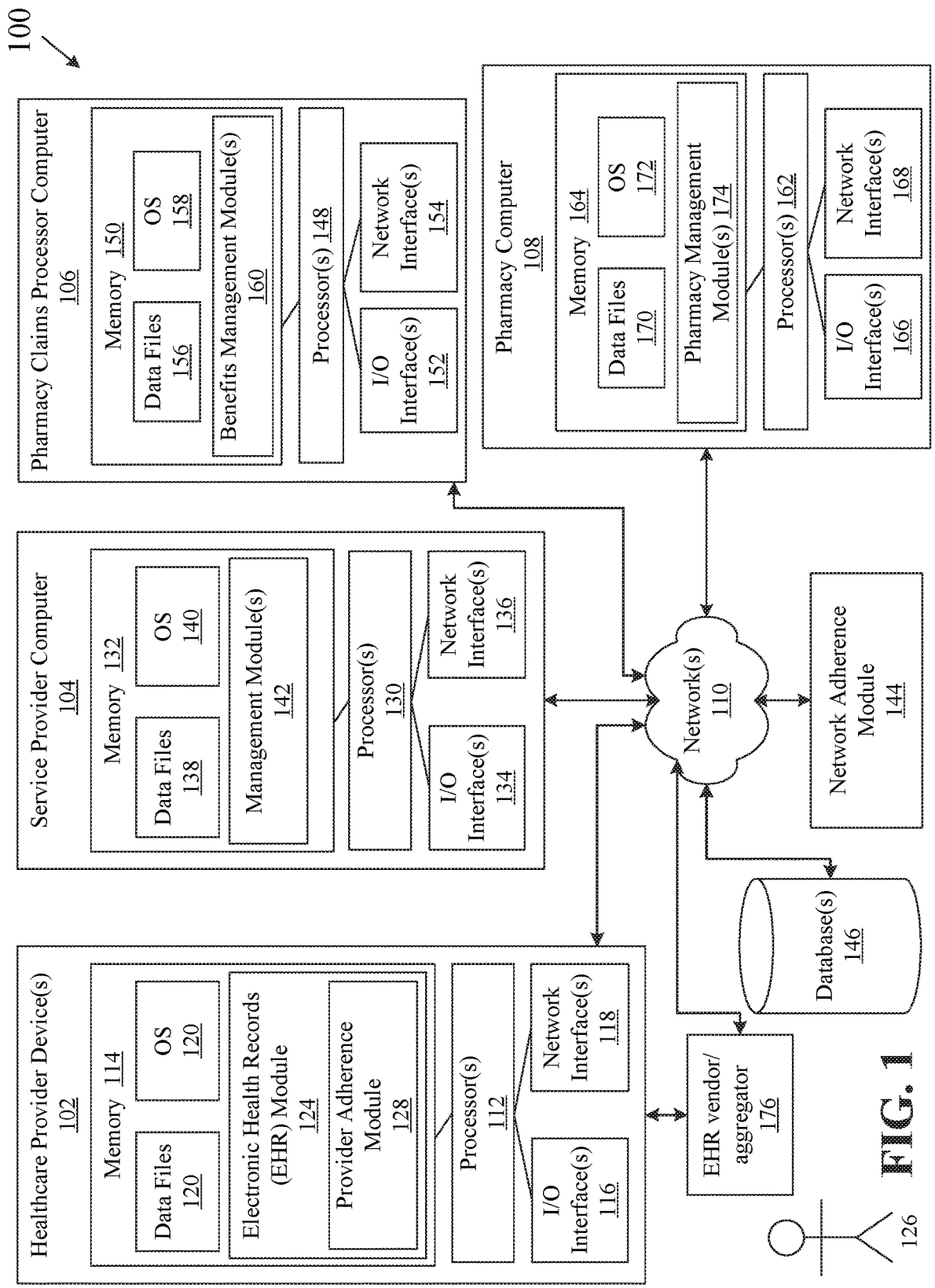
FIG. 1 illustrates an example overview of a system that facilitates the improved alternative therapy identification according to one exemplary embodiment.

Exemplary embodiments will now be described more fully hereinafter with reference to the accompanying drawings, in which example embodiments are shown. The concepts disclosed herein may, however, be embodied in many different forms and should not be construed as limited to the example embodiments set forth herein; rather, these embodiments are provided so that this disclosure will be thorough and complete, and will fully convey the scope of the concepts to those skilled in the art. Like numbers refer to like, but not necessarily the same or identical, elements throughout.

Example embodiments described herein include an improved alternative therapy identification system. In some example implementations, a prescription benefit check request may be communicated from a healthcare provider via a vendor computer. In one example, the prescription benefit check request may include pharmacy benefit information captured by a healthcare provider during a patient visit. For example, the healthcare provider may capture the patient's name, date of birth, gender, preferred pharmacy identification, and benefits provider identification. Additionally, the prescription benefit check request may include medication identification. In some examples, the prescription benefit check request may be communicated in real time or near real time to a service provider. The service provider may determine a request type associated with the prescription benefit check request type.

The service provider may communicate the prescription request (e.g., a prescription claim request, prescription billing request, or predetermination of benefits request) to the determined benefits provider. The benefits provider may process the request and communicate a response to the service provider. The response may include a status indicator to indicate whether the request is approved or denied as well as a field indicating a patient payment amount.

In one example, where the prescription benefit check request is denied, the service provider may automatically search for one or more alternative therapies available for the denied prescribed product. The service provider may select an alternative therapy based upon an average drug cost (e.g., a usual and customary cost) for one or more product identifiers (e.g., NDC) in a therapeutic class based upon claim data received from a pharmacy. The service provider may communicate an alternative therapy search request to the determined benefits provider. The benefits provider may process the request and communicate a response to the service provider. The response may include a status indicator to indicate whether the alternative request is approved or denied. Where the status indicator indicates an approved status, the response may also include a field indicating the patient payment amount. The service provider may communicate any alternative therapy information including patient payment amount to the healthcare provider.

By way of another example, the service provider computer may transmit a prescription benefit check response to the healthcare provider device that includes a denial of the prescribed product. The healthcare provider device may manually generate an alternative therapy search request, and communicate that search request to the service provider. The service provider may process the alternative therapy search request in a similar manner and communicate any alternative therapy information including patient payment amounts to the healthcare provider.

By way of yet another example, where the response indicates an approved status, the service provider may determine that a patient pay amount exceeds a patient payment threshold level. The service provider may select an alternative therapy based upon an average cost of a drug (e.g., a usual and customary cost) that does not result in a patient payment amount that exceeds patient payment threshold level for the specified therapeutic class. In one implementation, the average cost of each drug corresponds to the one or more product identifiers in a therapeutic class and may be based upon claim data previously received from a pharmacy and stored in one or more databases. The service provider may communicate a request to the determined benefits provider. The benefits provider may process the request and communicate a response to the service provider. The response may include a status indicator to indicate whether the request is approved or denied. Where the status indicator indicates an approved status, the response may also include a field indicating the patient payment amount. The service provider may communicate any alternative therapy information including patient payment amount to the healthcare provider.

By way of yet another example, the service provider computer may transmit a prescription benefit check response to the healthcare provider device that includes a patient payment amount for the prescribed product in the prescription benefit check request. The healthcare provider device may manually generate an alternative therapy search request based upon the patient payment amount exceeding a patient payment threshold level, and communicate that search request to the service provider for further processing.

System Overview

FIG. 1 illustrates an example system 100 supporting the improved adherence monitoring system, according to an example embodiment. As shown in FIG. 1, the system 100 may include at least one healthcare provider devices 102, service provider computers 104, pharmacy claims processor computer 106, pharmacy computer 108, alternative therapy module 144, and/or an EHR vendor/aggregator 176. As desired, each of the healthcare provider device 102, service provider computer 104, pharmacy claims processor computer 106, pharmacy computer 108, and/or alternative therapy module 144, may include one or more processing devices that may be configured for accessing and reading associated computer-readable media having stored thereon data and/or computer-executable instructions for implementing the improved adherence monitoring system.

Additionally, in certain exemplary embodiments, the service provider computer 104 and/or the alternative therapy module 144 may be in communication with one or more data storage devices, such as a database 146. The database 146 may receive, store, and provide, as needed, patient data and/or prescription data from the service provider computer 104 and/or the alternative therapy module 144. In certain exemplary embodiments, the prescription request data includes all or any portion of the data included in prescription requests received by the service provider computer 104 from a healthcare provider device 102 and/or processed prescription request responses processed by a pharmacy claims processor computer 106. Alternatively, the data storage function may be included in the service provider computer 104 and/or the alternative therapy module 144 themselves, such as in the memory 130 of the service provider computer 104.

Generally, network devices and systems, including one or more of the healthcare provider devices 102, service provider computers 104, alternative therapy module 144, pharmacy claims processor computer 106, and pharmacy computer 108 may include or otherwise be associated with suitable hardware and/or software for electronically transmitting and receiving data and/or computer-executable instructions over one or more communications links or networks. These network devices and systems may also include any number of processors for processing data and executing computer-executable instructions, as well as other internal and peripheral components that are well known in the art. Further, these network devices and systems may include or be in communication with any number of suitable memory devices operable to store data and/or computer-executable instructions. By executing computer-executable instructions, each of the network devices forms a special purpose computer or particular machine. As used herein, the term "computer-readable medium" describes any form of suitable memory or memory device.

As shown in FIG. 1, the healthcare provider device 102, service provider computer 104, pharmacy claims processor computer 106, pharmacy computer 108, alternative therapy module 144, database 146, and EHR vendor/aggregator 176 may be in communication with each other via one or more networks, such as network 110, which as described below can include one or more separate or shared private and public networks, including the Internet or a publicly switched telephone network. Each of these components, the healthcare provider device 102, service provider computer 104, pharmacy claims processor computer 106, pharmacy computer 108, alternative therapy module 144, database 146, EHR vendor/aggregator 176, and the network 110 will now be discussed in further detail.

Each healthcare provider device 102 may be associated with (e.g., located within and/or providing computing services for) a prescriber or other healthcare provider, such as, for example, a physician, physician's office, hospital, clinic, etc. Each healthcare provider device 102 may be any suitable processor-driven device that facilitates the processing of prescription benefit check requests made by or on behalf of a physician office for a patient prescription, the communication of healthcare requests to the service provider computer 104 via the EHR vendor/aggregator 176, and/or the receipt, processing, and display of responses received from the service provider computer 104 via the EHR vendor/aggregator 176. For example, the healthcare provider device 102, may be a computing device that includes any number of a server computers, a mainframe computers, one or more networked computers, a desktop computer, a personal computer, a digital assistant, a personal digital assistant, a digital tablet, an Internet appliance, an application-specific circuit, microcontroller, minicomputer, or any other processor-based device. The execution of the computer-implemented instructions by the healthcare provider computer 102 forms a special-purpose computer or other particular machine that is operable to facilitate the processing of prescription benefit check requests made by or on behalf of the physician's office and the communication of information associated with prescription benefit check requests to a healthcare provider device 102. Additionally, in certain example embodiments, the operations and/or control of each healthcare provider device 102 may be distributed amongst several processing components.

In addition to having one or more processors 112, each healthcare provider device 102 may include one or more memory devices 114, one or more input/output ("I/O")

interfaces 116, and one or more network interfaces 118. The memory devices 114 may be any suitable memory device, for example, caches, read-only memory devices, random access memory devices, magnetic storage devices, removable storage devices, etc. The memory devices 114 may store data, executable instructions, and/or various program modules utilized by the healthcare provider device 102, for example, data files 120, an operating system ("OS") 122, and/or an electronic health records (EHR) module 124, respectively. The data files 120 may include any suitable data that facilitates the receipt and/or processing of prescription benefit check requests by the healthcare provider device 102 and the generation and/or processing of prescription benefit check requests that are communicated to the service provider computer 104. For example, the data files 132 may include, but are not limited to, healthcare information and/or contact information associated with one or more patients, information associated with the particular healthcare provider and/or the respective healthcare provider device 102, information associated with the service provider computer 104, and/or information associated with one or more prescription benefit check requests. The OS 122 may be any suitable software module that controls the general operation of the healthcare provider computer 102. The OS 122 may also facilitate the execution of other software modules by the one or more processors 112, for example, the client module 124. The OS 122 may be any currently existing or future-developed operating system including, but not limited to, Microsoft Windows®, Apple OSX™, Linux, Unix, or a mainframe operating system.

The EHR module 124 may be a software application(s), including, but not limited to, a dedicated program: for making diagnoses, for determining prescriptions, over-the-counter medications, products or other healthcare services associated with one or more diagnoses; for creating prescription requests (including e-prescription requests (e.g., electronic prescription order requests, e-script, or e-prescription)); for reading and or updating medical records, as well as interacting with the service provider computer 104. For example, a user 126, such as a healthcare system employee, may utilize the EHR module 124 during a patient visit, for capturing the patient's pharmacy benefit information. Furthermore, the healthcare provider device 102 may utilize the EHR module 124 to retrieve or otherwise receive data, messages, or responses from the service provider computer 104 and/or other components of the system 100.

During the prescription process, the EHR module 124 may engage the provider adherence module 128 to communicate prescription information to the service provider computer 104. The provider adherence module 128 may gather all the required and available optional data including, but not limited to, the medication information, (e.g., total number of medications, medication name(s), NDC number(s), RxNorm, quantity, etc.), patient information (e.g., patient first and/or last name, gender, date of birth), and prescriber identification number (e.g., prescriber ID ((e.g., National Provider Identifier (NPI) number and/or a provider identification issued by the Drug Enforcement Agency (DEA), prescriber name, and prescriber ZIP code or other postal zone identifier. Following the information collection, the provider adherence module 128 formats one or more prescription requests (e.g., a predetermination of benefits requests, healthcare claim requests) for a patient prescription according to NCPDP telecom standards in the agreed upon format. The one or more prescription requests may be sent to the service provider computer 104 via the EHR vendor/aggregator 176.

The one or more I/O interfaces 116 may facilitate communication between the healthcare provider device 102 and one or more input/output devices, for example, one or more user interface devices, such as, a display, keypad, keyboard, control panel, touch screen display, remote control, mouse, microphone, etc. that facilitate user interaction with the healthcare provider device 102. For example, the one or more I/O interfaces 116 may facilitate entry of information associated with a prescription benefit check request by a healthcare provider such as a physician. The one or more network interfaces 118 may facilitate connection of the healthcare provider device 102 to one or more suitable networks, for example, the network 110 illustrated in FIG. 1. In this regard, the healthcare provider device 102 may receive and/or communicate information via the EHR vendor/aggregator 176 to other network components of the system 100, such as the service provider computer 104.

With continued reference to FIG. 1, the service provider computer 104 may include, but is not limited to, any suitable processor-driven device that is configured for receiving, processing, and fulfilling requests from the one or more healthcare provider devices 102, and/or the pharmacy claims processor computers 106. In certain exemplary embodiments, the service provider computer 104 may be a switch/router that routes prescription requests from a pharmacy to a pharmacy claims processor computer. For example, the service provider computer 104 may route prescription requests to a pharmacy claims processor computer 106, such as a pharmacy benefits manager (PBM), an insurer, a Medicare payor, other governmental healthcare insurance payor, or other third-party payor.

In certain embodiments, the service provider computer 104 may include a suitable host server, host module, or other software that facilitates the receipt of a prescription benefit check requests from a healthcare provider device 102 and/or the routing of prescription requests to a pharmacy claims processor computer 106. Any number of healthcare provider devices 102, alternative therapy modules 144, databases 146, and/or pharmacy claims processor computers 106 may be in communication with the service provider computer 104, via the network 110 for example, as desired in various embodiments.

The service provider computer 104 may include any number of special purpose computers or other particular machines, application-specific circuits, microcontrollers, personal computers, minicomputers, mainframe computers, servers, networked computers, and/or other processor-driven devices. In certain embodiments, the operations of the service provider computer 104 may be controlled by computer-executed or computer-implemented instructions that are executed by one or more processors 130 associated with the service provider computer 104 to form a special purpose computer or other particular machine that is operable to facilitate the receipt, routing, and/or processing of prescription benefit check requests and prescription requests. The one or more processors 130 that control the operations of the service provider computer 104 may be incorporated into the service provider computer 104 and/or in communication with the service provider computer 104 via one or more suitable networks. In certain exemplary embodiments, the operations and/or control of the service provider computer 104 may be distributed amongst several processing components.

Similar to the healthcare provider device 102 described above, the service provider computer 104 may include one or more processors 130, one or more memory devices 132, one or more input/output ("I/O") interfaces 134, and one or more network interfaces 136. The one or more memory devices 132 may be any suitable memory devices, for example, caches, read only memory devices, random access memory devices, magnetic storage devices, removable memory devices, etc. The one or more memory devices 132 may store data, executable instructions, and/or various program modules utilized by the service provider computer 104, for example, data files 138, an operating system ("OS") 140, a management module 142 to facilitate management of data files 138 and other data stored in the memory devices 132. The OS 138 may be a suitable software module that controls the general operation of the service provider computer 104 and/or that facilitates the execution of other software modules. The OS 138 may be any currently existing or future-developed operating system including, but is not limited to, Microsoft Windows®, Apple OSX™, Linux, Unix, or a mainframe operating system.

According to one exemplary embodiment, the data files 138 may store prescription request records and prescription benefit check request records associated with communications received from various healthcare provider devices 102, and/or various pharmacy claims processor computers 106, and/or various pharmacy computers 108. The data files 138 may also store any number of suitable routing tables that facilitate determining the destination of communications received from a healthcare provider device 102, and/or pharmacy claims processor computer 106. In certain example embodiments, the data discussed herein that is included in the database 146 may alternatively be stored and accessed from the data files 138. The exemplary data files 138 may also store records containing, for example, patient identification data, prescription requests, tables identifying pharmacies, prescribed product (e.g., medications, devices, etc.) or service identifiers, override codes, payor identifiers, and request type codes.

The management module 142 may be operable to perform one or more pre-edits or pre-analysis on a received prescription request prior to routing or otherwise electronically communicating the received prescription request to a suitable pharmacy claims processor computer 106. Additionally, the management module 142 may be operable to perform one or more post-edits on a processed response that is received from a pharmacy claims processor computer 108 for a prescription request prior to routing the processed prescription response to one of the healthcare provider devices 102. In one example embodiment, the management module may be operable to parse the prescription request and/or processed prescription request response to determine one or more of the pharmacy identifier, prescribed product (e.g., medications, devices, etc.) or vendor identifier, denial code/message, product/service cost, and request type code and can determine if the pharmacy identified by the pharmacy identifier, the prescribed product (e.g., medication, device, etc.), service, or medication class identified by the prescribed product or service identifier, the denial code or basis for denial, the product or service cost and/or the request type identified by the request type code.

The management module 142 may also receive, process, and respond to requests from the EHR module 124 and/or the provider adherence module 128 of the healthcare provider computer 102, may receive, process, and respond to requests of the alternative therapy module 144, may further receive, process, and respond to requests of the benefits management module 160 of the pharmacy claims processor computer 106. The service provider computer 104 may include additional program modules for performing other processing methods described herein. Those of ordinary skill in the art will appreciate that the service provider computer 104 may include alternate and/or additional components, hardware or software without departing from exemplary embodiments of the disclosure.

With continued reference to the service provider computer 104, the one or more I/O interfaces 134 may facilitate communication between the service provider computer 104 and one or more input/output devices, for example, one or more user interface devices, such as a display, keypad, keyboard, mouse, control panel, touch screen display, remote control, microphone, etc. that facilitate user interaction with the service provider computer 104. The one or more network interfaces 136 may facilitate connection of the service provider computer 104 to one or more suitable networks, for example, the network 110 illustrated in FIG. 1. In this regard, the service provider computer 104 may communicate with other components of the system 100.

One or more alternative therapy modules 144 may also be operative with or included with the service provider computer 104. The alternative therapy module 144 may include computer-executable instructions for facilitating the improved adherence monitoring system. In one example embodiment, the alternative therapy module 144 may be implemented as computer-implemented instructions of the memory 132 of the service provider computer 104. Alternatively, the alternative therapy module 144 may also be implemented as computer-implemented instructions of a memory of a separate processor-based system communicably coupled to the service provider computer 104, according to another example embodiment.

The database 146 of FIG. 1 represents one or more databases that can be locally or remotely distributed with respect to the service provider computer 104 and/or the alternative therapy module 144. The database 146 may be operable to store information associated with various patients and/or from various prescription requests that have been received by the service provider computer 104 and/or processed prescription request responses processed by the one or more pharmacy claims processor computers 106. The database 146 may also store one or more alternative treatment tables that include, without limitation, product identifiers (e.g., NDC), RxNorm, average cost corresponding to each product identifier (e.g., a usual and customary cost) based upon claim data received from the pharmacy computers 108 and/or the EHR vendor/aggregator 176, an average patient payment amount also based upon claim data received from the pharmacy computers and/or the EHR vendor/aggregator 176, and the like. The database 146 may further store one or more patient payment threshold levels aggregated via the EHR vendor/aggregator 176 and/or the pharmacy computers 108. In one implementation, the one or more patient payment threshold levels correspond to a patient payment threshold for a product prescribed by the prescriber for a particular therapeutic class (e.g., RxNorm).

With continued reference to FIG. 1, the pharmacy claims processor computer 106 (e.g., a pharmacy claims processor computer for a pharmacy computer) may be any suitable processor-driven device that facilitates receiving, processing, and/or fulfilling prescription requests received from the service provider computer 104. For example, the pharmacy claims processor computer 106 may be a processor-driven device associated with one or more PBMs, insurers, government payors, Medicare Part D payors, accountable care organizations, or claims clearinghouses. As desired, the pharmacy claims processor computer 106 may include any number of special purpose computers or other particular machines, application-specific circuits, microcontrollers, personal computers, minicomputers, mainframe computers, servers, and the like.

In certain exemplary embodiments, the operations of the pharmacy claims processor computer 106 may be controlled by computer-executed or computer-implemented instructions that are executed by one or more processors associated with the pharmacy claims processor computer 106 to form a special purpose computer or other particular machine that is operable to facilitate the receipt, processing, and/or fulfillment of prescription requests received from the service provider computer 104. The one or more processors that control the operations of the pharmacy claims processor computer 106 may be incorporated into the pharmacy claims processor computer 106 and/or in communication with the pharmacy claims processor computer 106 via one or more suitable networks. In certain embodiments, the operations and/or control of the pharmacy claims processor computer 106 may be distributed amongst several processing components.

Similar to other components of the system 100, the pharmacy claims processor computer 106 may include one or more processors 148, one or more memory devices 150, one or more input/output ("I/O") interfaces 152, and one or more network interfaces 154. The one or more memory devices 150 may be any suitable memory devices, for example, caches, read-only memory devices, random access memory devices, magnetic storage devices, removable memory devices. The one or more memory devices 150 may store data, executable instructions, and/or various program modules utilized by the pharmacy claims processor computer 106, for example, data files 156, an operating system ("OS") 158, and a benefits management module 160. The data files 156 may include any suitable information that is utilized by the pharmacy claims processor computer 106 to process prescription requests, for example, patient profiles, patient insurance information, other information associated with a patient, information associated with a healthcare provider, etc. The OS 158 may be a suitable software module that controls the general operation of the pharmacy claims processor computer 106. The OS 158 may also facilitate the execution of other software modules by the one or more processors 148, for example, the benefits management module 160. The OS 158 may be any currently existing or future-developed operating system including, but is not limited to, Microsoft Windows®, Apple OSX™, Linux, Unix, or a mainframe operating system.

The benefit management module 160 may be a suitable software module that facilitates access and management of one or more databases that are utilized to store information that is utilized by the pharmacy claims processor computer 106 in various example embodiments. The benefits management module may also initiate, receive, process, and/or respond to requests, such as prescription requests, from the management module 140 of the service provider computer 104. The pharmacy claims processor computer 106 may include additional program modules for performing other pre-processing or post-processing methods described herein. Those of ordinary skill in the art will appreciate that the pharmacy claims processor computer 106 may include alternate and/or additional components, hardware or software without departing from the example embodiments described herein.

The one or more I/O interfaces 152 may facilitate communication between the pharmacy claims processor computer 106 and one or more input/output devices, for example, one or more user interface devices, such as a display, keypad, keyboard, mouse, control panel, touch screen display, remote control, microphone, etc. that facilitate user interaction with the pharmacy claims processor computer 106. The one or more network interfaces 154 may facilitate connection of the pharmacy claims processor computer 106 to one or more suitable networks, for example, the network 110. In this regard, the pharmacy claims processor computer 106 may receive prescription requests and/or other communications from the service provider computer 104 and the pharmacy claims processor computer 106 may communicate information associated with processing the prescription requests and providing responses to the service provider computer 104.

With continued reference to FIG. 1, any number of pharmacy computers 108 may be associated with any number of pharmacies and/or pharmacists. Each pharmacy computer 108 may be any suitable processor-driven device that facilitates receiving electronically, processing, and/or fulfilling healthcare requests and/or prescription requests electronically received from the service provider computers 104. For example, a pharmacy computer 108 may be a processor-driven device associated with (i.e., located within) a pharmacy. As desired the pharmacy computer 108 may include any number of special-purpose computers or other particular machines, application-specific integrated circuits, microcontrollers, personal computers, minicomputers, mainframe computers, servers, and the like. In certain example embodiments, the operations of the pharmacy computer 108 may be controlled by computer-executed or computer-implemented instructions that are executed by one or more processors associated with the pharmacy computer 108 to form a special-purpose computer or other particular machine that is operable to facilitate the generation, processing, and/or fulfillment of prescription requests electronically transmitted to the service provider computer 104. The one or more processors that control the operations of a pharmacy computer 108 may be incorporated into the pharmacy computer 108 and/or may be in communication with the pharmacy computer 108 via one or more suitable networks. In certain example embodiments, the operations and/or control of the pharmacy computer 108 may be distributed among several processing components.

Similar to other components of the system 100, each pharmacy computer 108 may include one or more processors 162, one or more memory devices 164, one or more I/O interfaces 166, and one or more network interfaces 168. The one or more memory devices 164 may be any suitable memory devices, for example, caches, read-only memory devices, random access memory devices, magnetic storage devices, removable memory devices, etc. The one or more memory devices 164 may store data, executable instructions, and/or various program modules utilized by the pharmacy computer 108, for example, data files 170, an OS 172, and a pharmacy management module 174. The data files 170 may include any suitable information that is utilized by the pharmacy computer 108. The OS 172 may be a suitable software module that controls the general operation of the pharmacy computer 108. The OS 172 may also facilitate the execution of other software modules by the one or more processors 162. The OS 172 may be any currently existing or future-developed operating system including, but is not limited to, Microsoft Windows®, Apple OSX™, Linux, Unix, or a mainframe operating system.

The one or more I/O interfaces 166 may facilitate communication between the pharmacy computer 108 and one or more input/output devices, for example, one or more user interface devices, such as a display, keypad, control panel, touch screen display, remote control, microphone, etc., that facilitate user interaction with the pharmacy computer 108. The one or more suitable network interfaces 168 may facilitate connection of the pharmacy computer 108 to one or more suitable networks, for example, the network 110 illustrated in FIG. 1. In this, the pharmacy computer 108 may electronically receive healthcare requests and/or communications from the service provider computer 104 and the pharmacy computer 108 may communicate information associated with processing healthcare requests to the database 146. For example, information included in one or more healthcare requests (e.g., claim data) may be stored in the database 146 for use by the service provider 104. In one implementation, the claim data may be used to identify an alternative therapy (e.g., medication, product, etc.) during those processes described herein.

The pharmacy management module 174 may be a software application(s) including a dedicated program, for fulfilling healthcare request orders, reading and/or updating medical records (e.g., prescription records, facilitating patient billing, etc., as well as interacting with the service provider 104. For example, a pharmacist or other pharmacy employee, may utilize the pharmacy management module 174 in filling a prescription, recording and/or updating a patient's medical prescription history, billing a prescription, and preparing and providing a healthcare request for information to the service provider computer 104. Furthermore, the pharmacy computer 108 may utilize the pharmacy management module 174 to retrieve or otherwise electronically receive data, messages, or response from the healthcare provider device 102 and/or other components of the system 100.

With continued reference to FIG. 1, the system 100 may include any number of EHR vendor(s)/aggregator(s) 176. Each EHR vendor/aggregator 176 may be associated with any number of healthcare provider devices and computer systems 102 and may provide an electronic communications channel or pipeline between each respective healthcare provider device 102 and the service provider computer 104 via the network 110. In certain example embodiments, the EHR vendor/aggregator 176 provides a single-point access for the transmission of data and requests associated with or using a healthcare provider's electronic medical records system to the service provider computer 104 via the healthcare provider device 102. Furthermore, the EHR vendor/aggregator 176 may also provide access for the transmission of data and responses from the service provider computer 104 to the healthcare provider device 102. Each EHR vendor/aggregator 176 may also aggregate data received from multiple healthcare provider devices, pharmacy claims processor computers, and/or pharmacy computers for subsequent access by the healthcare provider device 102 and/or the service provider computer 104.

The network 110 may include any telecommunication and/or data network, whether public, private, or a combination thereof, including a local area network, a wide area network, an intranet, the Internet, intermediate hand-held data transfer devices, and/or any combination thereof and may be wired and/or wireless. The network 110 may also allow for real-time, off-line, and/or batch transactions to be electronically transmitted between or among the healthcare provider device 102, the service provider computer 104, the alternative therapy module 144, the database 146, and/or the pharmacy claims processor computer 106. Due to network connectivity, various methodologies, as described herein may be practiced in the context of distributed computing environments. Although the service provider computer 104 is shown for simplicity as being in communication with the healthcare provider device 102, the alternative therapy module 144, the database 146, and/or the pharmacy claims processor computer 106 via one intervening network 110, it is to be understood that any other network configuration is possible. For example, intervening network 110 may include a plurality of networks, each with devices such as gateways and routers for providing connectivity between or among networks 110. Instead of or in addition to a network 110, dedicated communication links may be used to connect the various devices in accordance with an example embodiment. For example, the service provider computer 104 may form the basis of network 110 that interconnects one or more of the healthcare provider device 102, the alternative therapy module 144, the database 146, and the pharmacy claims processor computer 106.

Those of ordinary skill in the art will appreciate that the system 100 shown in and described with respect to FIG. 1 is provided by way of example only. Numerous other operating environments, system architectures, and device configurations are possible. Other system embodiments can include fewer or greater numbers of components and may incorporate some or all of the functionality described with respect to the system components shown in FIG. 1. For example, in one exemplary embodiment, the service provider computer 104 (or other computer) may be implemented as a specialized processing machine that includes hardware and/or software for performing the methods described herein. Accordingly, the exemplary embodiments described herein should not be construed as being limited to any particular operating environment, system architecture, or device configuration.

Operational Overview

Figure 2A:
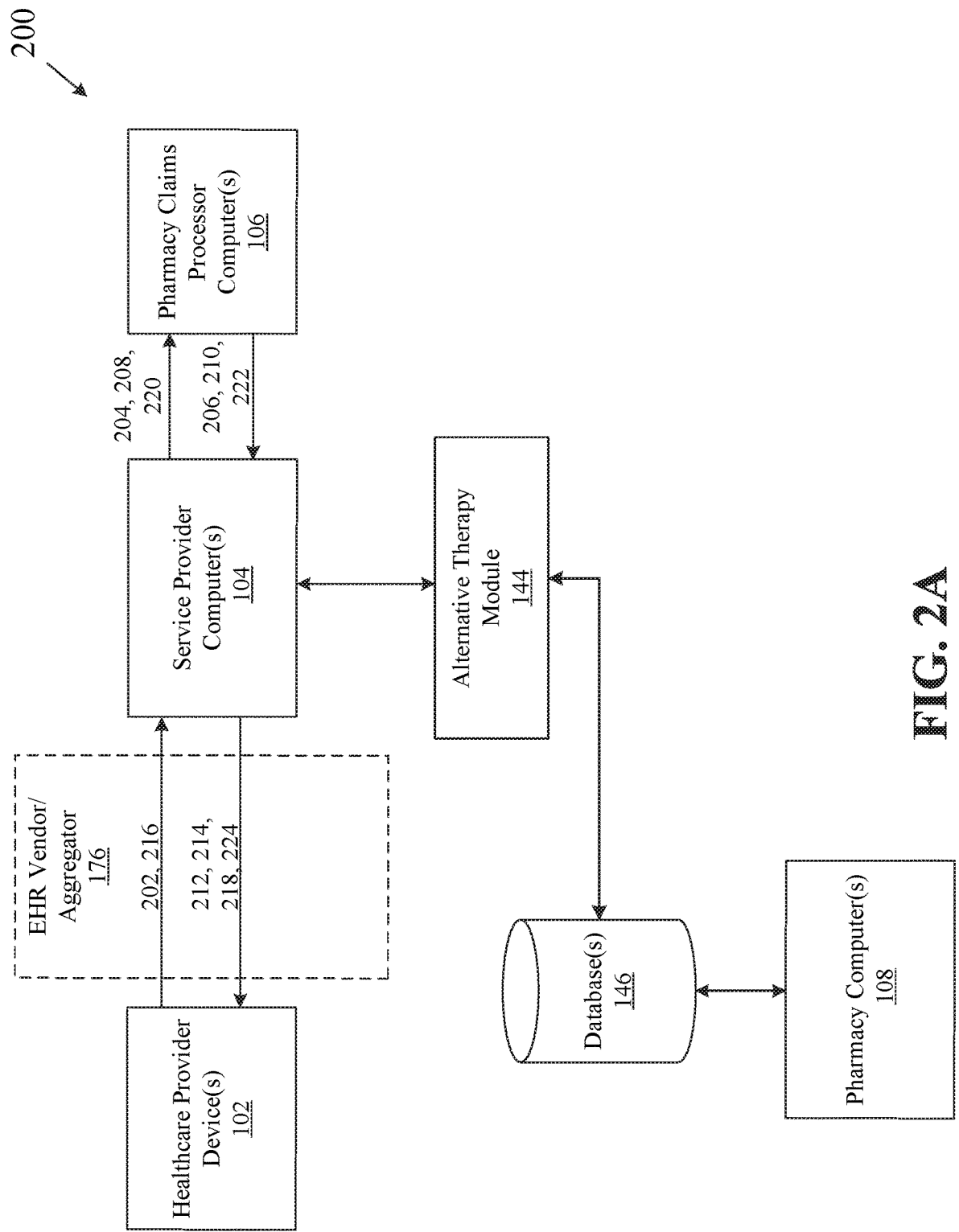
FIG. 2A is a diagram of an example system flow for providing improved alternative therapy identification according to one exemplary embodiment.
Figure 3:
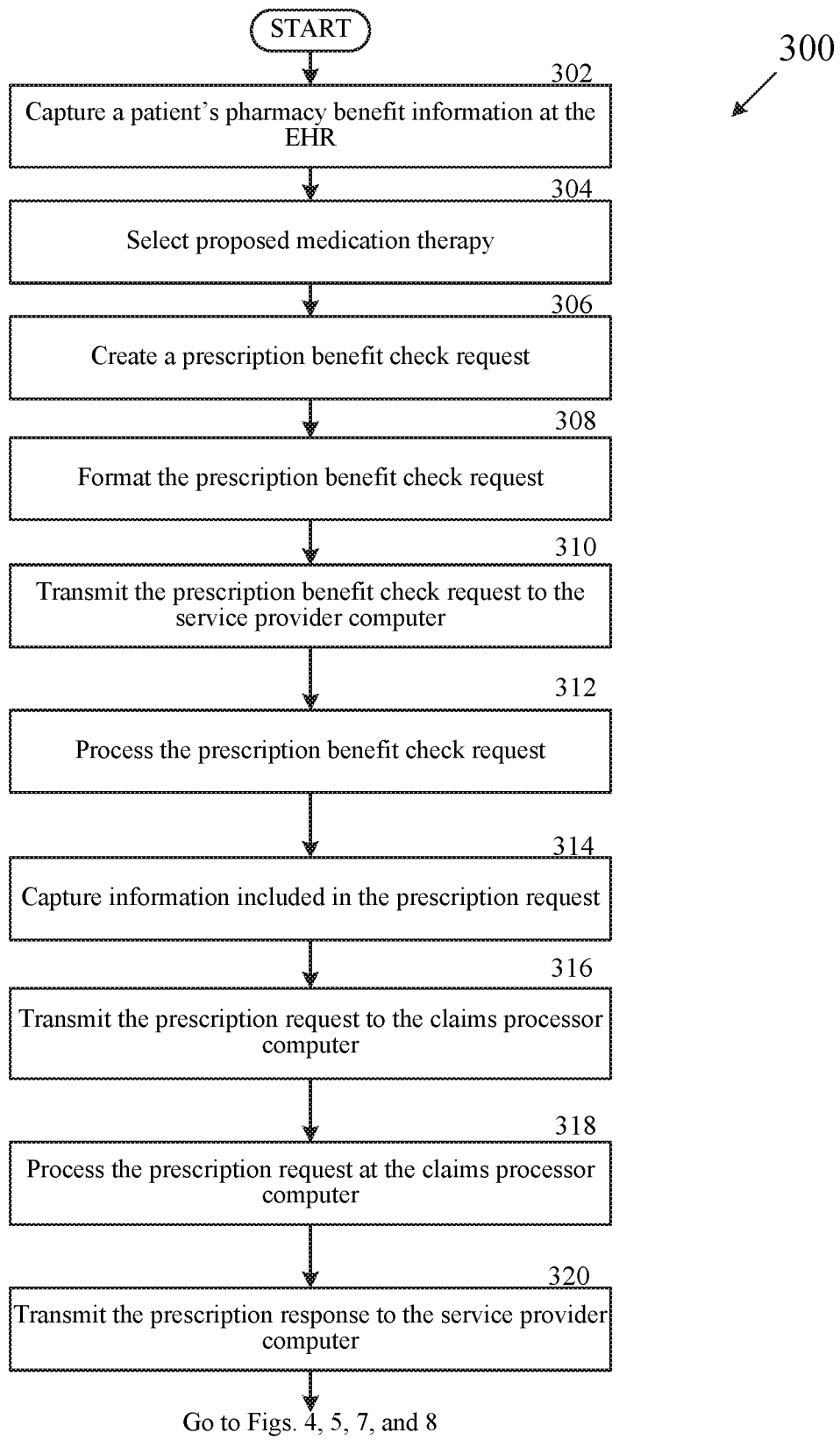
FIG. 3 is an exemplary methodology for implementing the improved alternative therapy identification system, in accordance with one exemplary embodiment.

FIG. 2A is a diagram of one example data flow 200 for the improved alternative therapy system as part of or in-line with the processing of a prescription benefit check requests and prescription requests through a service provider, such as through the service provider computer 104 illustrated in FIG. 1. FIG. 3 is a flow chart of an example method 300 for implementing the improved alternative therapy identification system as part of the processing of the prescription benefit check request and prescription request in accordance with one exemplary embodiment. The exemplary method 300, described below, may be performed by a suitable service provider computer 104 and/or alternative therapy module 144.

The exemplary method 300 will be described with reference to a prescriber as the healthcare provider; however, this is only for purposes of example as other healthcare providers could be substituted for, and should each be individually read as being a part of each of these methods. As such, where the discussion of the methods below and the drawings state a physician, any other healthcare provider could be substituted, such as a physician, hospital, physician's office, clinic, prescriber of the medication, or healthcare center.

In addition, the exemplary method 300 described below will be described with reference to a prescription request as the healthcare claim request; however, this also is only for purposes of example as other prescription requests (which may include, for example, a prescription claim request, prescription billing request, or predetermination of benefits request) could be substituted for the prescription request and each form of prescription request should each individually be read as being used in the methods described below Referring now to FIGS. 1, 2A, and 3, the exemplary method 300 begins at the START step and proceeds to step 302, where the healthcare provider device, such as the healthcare provider device 102, may be utilized to capture a patient's pharmacy benefit information. In one example implementation, the healthcare provider device 102 may employ an electronic health records (EHR) module 124 to capture the patient's pharmacy benefit information. The patient's pharmacy benefit information may be captured as a part of patient visit. For example, the patient's pharmacy benefit information may be captured as a part of an administrative function at the point of a patient admission (e.g., a patient registration). Alternatively, the patient's pharmacy benefit information may be captured at a time other than the patient visit. For example, the patient may communicate pharmacy benefit information utilizing a web-based portal from any patient desired location. Generally, the patient pharmacy benefit information may be found on a patient's pharmacy benefit card (e.g., patient insurance card). For example, without limitation, the EHR module 124 may capture from a patient's pharmacy benefit card, a BIN number, a processor control number, an assigned cardholder ID, person code, relationship code, and/or a group ID. Additional patient information not generally included on the patient's pharmacy benefit card that may be captured by the EHR includes, without limitation a patient's date of birth and/or a patient gender code.

At step 304, a prescriber may select a proposed medication therapy. The proposed medication therapy may include a medication identifier (e.g., a National Drug Code (NDC) identification, RxNorm medication identifiers, a medication name, and the like). At step 306, the healthcare provider device 102 creates a prescription benefit check request 202. In one implementation, the healthcare provider device 102 may employ a provider adherence module 128 to create the prescription benefit check request. The prescription benefit check request 202 may include, without limitation, the patient pharmacy benefit information, and/or prescriber information. In one example implementation, the prescription benefit check request 202 may include one or more optional fields. For example, the prescription benefit check request 202 may include, without limitation, the medication identifier, a total number of medications selected by the prescriber, the BIN number, the processor control number, a service provider ID (e.g., a patient's pharmacy of choice), the cardholder ID, the group ID, the person code, the patient's date of birth, the patient's gender code, the patient's first and/or last name, a product service ID, a prescriber ID, and/or a prescriber last name.

At step 308, the healthcare provider device 102 may format the prescription benefit check request 202. In one example implementation, the healthcare provider device 102 may employ the provider adherence module 128 to format the prescription benefit check request 202. According to one example embodiment, the healthcare request 202 may be formatted in accordance with a version of the National Council for Prescription Drug Programs (NCPDP) Telecommunication Standard, although other standards may be utilized as well.

As discussed above, the prescription benefit check request 202 may include a BIN Number, a BIN Number and PCN, and/or a BIN Number and Group ID for identifying a particular pharmacy claims processor computer (e.g., PBM, healthcare insurance company, Medicare or other government healthcare insurance payor, Medicare Part D provider, etc.), such as the pharmacy claims processor computer 106, as a destination for the prescription benefit check request 202. In addition, the prescription benefit check request 202 may also include information relating to the patient, payor, prescriber, healthcare provider, and/or the requested product (e.g., medication or device) or service. As an example, the prescription benefit check request 202 may include one or more of the following information:

Payor identifier—Payor ID/Routing Information
BIN Number (i.e. Banking Identification Number), BIN Number and Processor Control Number (PCN) and/or BIN Number and Group ID, that designates a destination (e.g., the pharmacy claims processor computer 106) of the prescription benefit check request 202
Patient Information
Name (e.g. Patient Last Name, Patient First Name, etc.)
Date of Birth of Patient
Age of Patient
Gender
Patient Address (e.g. Street Address, Zip Code, etc.)
Patient Contact Information (e.g. patient telephone number, email address, etc.)
Patient Health Condition Information
Patient ID or other identifier (e.g., Health Insurance Claim Number (HICN), social security number, etc.)
Insurance/Coverage Information
Cardholder Name (e.g. Cardholder First Name, Cardholder Last Name)
Cardholder ID and/or other identifier (e.g. person code)
Group ID and/or Group Information
Prescriber Information
Primary Care Provider ID or other identifier (e.g. NPI code)
Primary Care Provider Name (e.g. Last Name, First Name)
Prescriber ID or other identifier (e.g. NPI code, DEA number)
Prescriber Name (e.g. Last Name, First Name)
Prescriber Contact Information (e.g. Telephone Number)
Prescriber Address (e.g., street address, city, state, zip code)
Pharmacy Information
Pharmacy or other Healthcare Provider Information (e.g. store name, chain identifier, etc.)
Pharmacy address (e.g., Street Address, Zip Code, etc.)
Pharmacy or other Healthcare Provider ID (e.g. NPI code)
Claim Information
Medication, service, or product information—Product (medication or device) or service identifier (e.g. National Drug Code (NDC code), RxNorm code, etc.), product or service name, etc.
Prescription/Service Reference Number
Date Prescription Written
Quantity Dispensed
Days' Supply
Diagnosis/Condition (e.g., diagnosis code)
Pricing information for the drug/service/product (e.g. ingredient cost (e.g., in an Ingredient Cost field), dispensing fee (e.g., in a Dispensing Fee field), gross amount due (e.g., in a Gross Amount Due field), and Usual and Customary Charge amount (e.g., in a Usual and Customary Charge field))
Number of Refills Authorized
Fill Number (i.e., the current refill number for the prescription benefit check request 202)
One or more NCPDP Message Fields
One or more Drug Utilization (DUR) Codes
Date of Service.

The prescription benefit check request 202 can be used to determine if the pharmacy claims processor associated with the pharmacy claims processor computer 106 approves or denies payment coverage for the prescribed product (e.g., medications, devices, etc.) or service being requested in the prescription benefit check request 202 and, if approved, the amount the pharmacy claims processor will cover (or pay) for the prescribed product (e.g., medication, device, etc.) or service being requested and how much the patient pay amount (the amount the patient is responsible to pay for) will be.

The healthcare provider device 102 electronically transmits the prescription benefit check request 202 to the service provider computer 104 via EHR vendor/aggregator 176 in step 310. At step 312 the service provider computer 104 may process the prescription benefit check request 202. For example, the service provider computer 104 can parse the received prescription benefit check request 202 to determine the destination of the prescription benefit check request 202 (e.g., based on the Banking Identification Number (BIN Number), the BIN Number and Processor Control Number (PCN) or the BIN Number and Group ID in one or more fields of the prescription benefit check request 202).

Processing of the prescription benefit check request 202 may also include identifying a request type. For example, based upon the determination of the destination pharmacy claims processor computer 106, a prescription request 204 may be determined to be a billing request "B1", a predetermination of benefits request "D1", and/or a request type not supported by the system FIG. 1.

At step 314, the service provider 104 may capture information included in the one or more fields of the prescription request 204. For example, without limitation, the alternative therapy module 144 or another portion of the service provider computer 104 may capture, without limitation, a RxNorm, the medication identifier, a total number of medications selected by the prescriber, the BIN number, the processor control number, a service provider ID (e.g., a patient's pharmacy of choice), the cardholder ID, the group ID, the person code, the patient's date of birth, the patient's gender code, the patient's first and/or last name, a product service ID, a prescriber ID, and/or a prescriber last name. The information captured in the prescription request 204 may be stored in the database 146 and or the data files 138.

The service provider computer 104 electronically transmits the prescription request 204 to the pharmacy claims processor computer 106 in step 316. For example, a prescription request 204 can be electronically transmitted from the service provider computer 104 to the pharmacy claims processor computer 106 via the network 110. The pharmacy claims processor computer 106 receives and processes the prescription request in step 318 to determine if the patient has coverage, to determine to what extent the patient's coverage covers the requested product or service identified in the request 204, and to generate a prescription response 206 as to whether the request 204 is approved or denied. Example responses in the prescription response 206 can include, but are not limited to, accepted, approved, captured, denied (e.g., rejected), and denied (e.g., rejected) with request for additional information and resubmission. In certain exemplary embodiments, the responses can be input into a field of the prescription request 204 that is recognized by the service provider computer 104 and/or the healthcare provider computer 102. Typically, if the response for the request 204 is approved, the prescription response 206 provides the amount of the cost of the medication, product, or service that will be covered by the pharmacy claims processor computer 106 (the total amount paid, which is provided in the Total Amount Paid field of the prescription response 206), any amount applied to a patient deductible which is provided in the amount applied to periodic deductible field of the prescription response 206), the patient pay amount (which is provided in the Patient Pay Amount field of the prescription response 206), a pharmacy name field populated with a short pharmacy name corresponding to the submitted service provider ID on the prescription request 204, and/or a pharmacy street address populated with a pharmacy street address corresponding to the submitted service provider ID on the prescription request 204. On the other hand, if the response is a denial (e.g., rejection), the prescription response 206 provides the reason for the denial (e.g., in the form of a denial code, for example, patient not covered, Cardholder ID submitted in the request is inactive, prior authorization required, medication not covered, claim limit exceeded, quantity exceeded, days' supply exceeded, etc.).

In step 320, the pharmacy claims processor computer 106 electronically transmits the prescription response 206 to the service provider computer 104 via, for example, the network 110.

Following step 320, processing of the prescription response may continue to the processes described in FIGS. 4, 5, 7, and 8 for identifying an alternative therapy.

Figure 4:
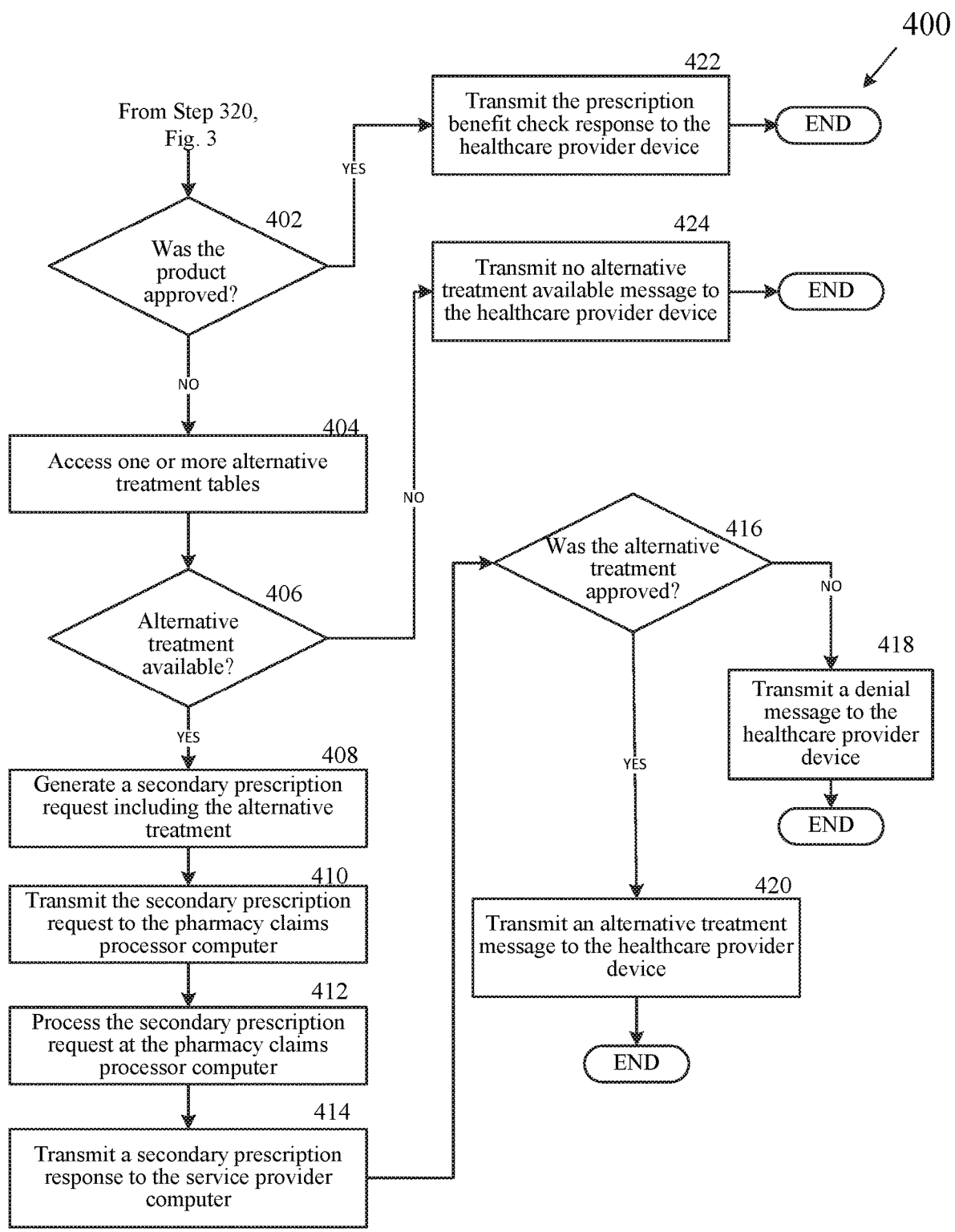
FIG. 4 is another example methodology for providing improved alternative therapy identification according to one exemplary embodiment.

FIG. 4 is a flow chart of an example method 400 for implementing the improved alternative therapy identification system described with reference to FIG. 3 as part of the processing of the prescription request in accordance with one exemplary embodiment. The exemplary method 400, described below, may be performed by a suitable service provider computer 104 and/or alternative therapy module 144.

Referring now to FIGS. 1, 2A, 3, and 4 the exemplary method 400 begins at the START step and proceeds to step 402, where the alternative therapy module 144 or another portion of the service provider computer 104 may determine whether the product in the prescription response 206 was approved by the pharmacy claims processor (e.g., the pharmacy claims processor 106). In one example, the alternative therapy module 144 may identify a status of the prescription response 206 as an approved status or as a denied status. In one example implementation, the status may be identified based upon a status indicator in a field in the prescription response 206. If the product in the prescription response 206 was denied, the NO branch is followed to step 404. On the other hand, if the product in the prescription 206 was approved, the YES branch is followed to step 422.

At step 404, the alternative therapy module 144 or another portion of the service provider module 104 may access one or more alternative treatment tables. In one implementation, the one or more alternative treatment tables may be stored in database 146. Alternatively and/or additionally, the one or more alternative treatment tables may be stored in data files 138 of the service provider computer 104. In one implementation, the each of the alterative treatment tables may be set up at a pharmacy chain/group level based upon data received at least from the pharmacy computers 108. For example, a first alternative treatment table may correspond to a CVS pharmacy chain, a second alternative treatment table may correspond to a Bartell Drug pharmacy chain, a third alternative treatment table may correspond to a Walgreens pharmacy chain, etc. Each alternative treatment table may, in one implementation, include claim data received from one or more pharmacy computers associated with each of the pharmacy chains (e.g., pharmacy computer 108). The claim data received from the pharmacy computer may be organized in the one or more alternative treatment tables by RxNorm (e.g., identifying a therapeutic class) and may include, without limitation, one or more product identifiers (e.g., NDC number), and at least historical data providing an average drug cost (e.g., usual and customary cost) corresponding to each product identifier. Accordingly, accessing the one or more alternative treatment tables may provide information corresponding to a lowest drug cost for multiple products (e.g., NDCs) within a same RxNorm based the upon claim data (e.g., historical claim data) received from the pharmacy computer and stored in a database, such as database 146. While each of the alternative tables is described as corresponding to a pharmacy chain, it is to be appreciated that the alternative tables may be set up at another group level (e.g., a vendor group level, etc.).

At step 406, the alternative therapy module 144 or another portion of the service provider module 104 may query the one or more alternative treatment tables to determine whether an alternative treatment is available for the product denied in the prescription response 206. In one implementation, the alternative therapy module 144 may search for an alternative treatment table corresponding to the pharmacy name field in the prescription response 206 populated with a short pharmacy name corresponding to the submitted service provider ID on the prescription request 204. The alternative therapy module 144 may parse the identified alternative treatment table for the RxNorm and/or NDC in the prescription response 206 and/or in the corresponding prescription request 204. Once the appropriate RxNorm and/or NDC has been identified, the alternative therapy module 144 may search the historical data to identify an alternative product that corresponds to a lowest drug cost (e.g., based upon the usual and customary cost) for that particular pharmacy chain/group. For example, the prescription response 206 may identify the pharmacy name as a CVS pharmacy. The denied NDC may correspond to the product Lisinopril, a tablet dosage form within the therapeutic class of ACE inhibitors. The alternative therapy module 144 may search within the same therapeutic class of ACE inhibitors to identify one or more available alternative dosage forms as well as a corresponding drug cost for the alternative dosage form for the CVS pharmacy chain. For example, the alternative therapy module may identify the product Benazepril, also a tablet dosage form ACE inhibitor with the lowest drug cost. If an alternative treatment is identified, the YES branch is followed to step 408. On the other hand, if no alternative treatment is identified, the NO branch is followed to step 424.

At step 408, the service provider computer 104 may generate a secondary prescription request 208. In one implementation, the secondary prescription request 208 may be formatted in accordance with a version of the National Council for Prescription Drug Programs (NCPDP) Telecommunication Standard, although other standards may be utilized as well as described herein with respect to prescription request 204. The service provider computer 104 electronically transmits the secondary prescription request 208 to the pharmacy claims processor computer 106 in step 410. For example, a secondary prescription request 208 can be electronically transmitted from the service provider computer 104 to the pharmacy claims processor computer 106 via the network 110.

The pharmacy claims processor computer 106 receives and processes the secondary prescription request in step 412 to determine if the patient has coverage, to determine to what extent the patient's coverage covers the requested product or service identified in the request 208, and to generate a secondary prescription response 210 as to whether the request 208 is approved or denied/rejected. As described herein with respect to response 206, example responses in the secondary prescription response 210 can include, but are not limited to, accepted, approved, captured, denied (e.g., rejected), and denied (e.g., rejected) with request for additional information and resubmission. In certain exemplary embodiments, the responses can be input into a field of the secondary prescription request 208 that is recognized by the service provider computer 104 and/or the healthcare provider computer 102. Typically, if the response for the request 208 is approved, the secondary prescription response 210 provides the amount of the cost of the medication, product, or service that will be covered by the pharmacy claims processor computer 106 (the total amount paid, which is provided in the Total Amount Paid field of the secondary prescription response 210), any amount applied to a patient deductible which is provided in the amount applied to periodic deductible field of the secondary prescription response 210), the patient pay amount (which is provided in the Patient Pay Amount field of the secondary prescription response 210), a pharmacy name field populated with a short pharmacy name corresponding to the submitted service provider ID on the secondary prescription request 208, and/or a pharmacy street address populated with a pharmacy street address corresponding to the submitted service provider ID on the secondary prescription request 208. On the other hand, if the response is a denial, the secondary prescription response 210 provides the reason for the denial (e.g., in the form of a denial code, for example, patient not covered, Cardholder ID submitted in the request is inactive, prior authorization required, medication not covered, claim limit exceeded, quantity exceeded, days' supply exceeded, etc.).

At step 414, the pharmacy claims processor computer 106 electronically transmits the secondary prescription response 210 to the service provider computer 104 via, for example, the network 110. At step 416, the alternative therapy module 144 or another portion of the service provider computer 104 may determine whether the product in the secondary prescription response 210 was approved by the pharmacy claims processor (e.g., the pharmacy claims processor 106). In one example, the alternative therapy module 144 may identify a status of the secondary prescription benefit check response 210 as an approved status or as a denied status. In one example implementation, the status may be identified based upon a status indicator in field in the secondary prescription response 210. If the alternative treatment was denied, the NO branch is followed to step 418. On the other hand, if the alternative treatment was approved, the YES branch is followed to step 420.

If the alternative treatment is denied by the pharmacy claims processor computer 106, at step 418, the service provider computer 104 may transmit a denial message to the healthcare provider device 102 via EHR vendor/aggregator 176. In one implementation, a prescription benefit check response 212 may include the denial message, which includes, without limitation, denial information from the secondary prescription response 210. For example, denial information from the secondary prescription response 210 may be inserted into a field (e.g., a text field) of the prescription benefit check response 212. Alternatively, the secondary prescription benefit check response 212 may be appended or otherwise electronically transmitted with the prescription response 210. The process then continues to the END step.

However, if the alternative treatment was approved by the pharmacy claims processor computer 106, the service provider computer 104 may transmit an alternative treatment message to the healthcare provider device 102 via EHR vendor/aggregator 176. In one implementation, the prescription benefit check response 212 may include the alternative treatment message which includes, without limitation, the NDC, RxNorm, patient pay amount, etc. from the secondary prescription response 210. For example, the alternative treatment information may be inserted into a field (e.g., a text field) of the prescription benefit check response 212. Alternatively, the secondary prescription benefit check response 212 may be appended or otherwise electronically transmitted with the prescription response 210. The process then continues to the END step.

If at step 402 the product in the prescription response 206 was approved, the prescription benefit check response 212 may be electronically transmitted to the healthcare provider device 102 via EHR vendor/aggregator 176. The process then continues to the END step.

If at step 406 no alternative treatments were identified for the denied prescribed product, the service provider computer 104 may transmit a no alternative treatment available message to the healthcare provider device 102 via EHR vendor/aggregator 176. In one implementation, the prescription benefit check response 212 may include the no alternative treatment available message. For example, the no alternative treatment available message may be inserted into a field (e.g., a text field) of the prescription benefit check response 212. The process then continues to the END step.

While the flow chart described with respect to FIG. 4 illustrates the process ending following the second request/response, it is to be appreciated that subsequent requests/responses may be generated.

Figure 5:
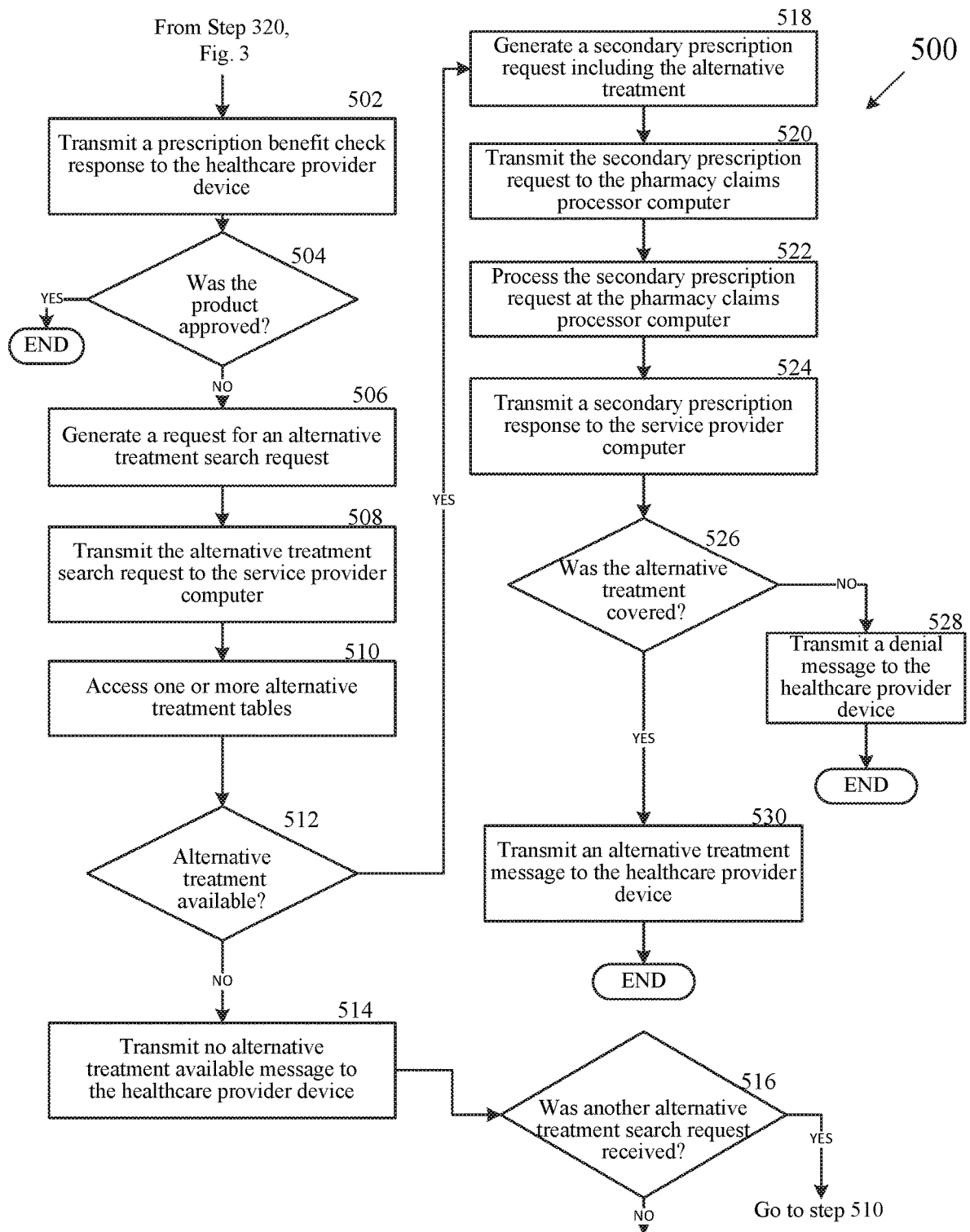
FIG. 5 is another example methodology for providing improved alternative therapy identification according to one exemplary embodiment.

FIG. 5 is a flow chart of an example method 500 for implementing the improved alternative therapy identification system described with reference to FIGS. 2A and 3 as part of the processing of the prescription request in accordance with one exemplary embodiment. The exemplary method 500, described below, may be performed by a suitable service provider computer 104 and/or alternative therapy module 144.

Referring now to FIGS. 1, 2A, 3, and 5 the exemplary method 500 begins at the START step and proceeds to step 502, where the service provider computer 104 may electronically transmit a prescription benefit check response 214 to the healthcare provider device 102 via EHR vendor/aggregator 176. At step 504, the healthcare provider device 102 may determine whether the prescription benefit check response 214 includes an approved status indicator or a denied status indicator. If the prescription benefit check response 214 includes an approved status indicator, the YES branch is followed and the process may end after step 504. If on the other hand the prescription benefit check response 214 includes a denied status indicator, the NO branch is followed and the process may continue to step 506.

At step 506, the user (e.g., user 126) of the healthcare provider device 102 may generate a request for an alternative treatment search 210. The alternative treatment search request 216 may include, without limitation, information included in the original prescription benefit check request 202, for example, the patient's pharmacy information (e.g., Service Provider ID, pharmacy name, pharmacy address, etc.) a RxNorm indicating the desired therapeutic class, BIN number, patient identification information, etc.

At step 508, the healthcare provider device 102 electronically transmits the alternative treatment search request 216 to the service provider computer 104 via EHR vendor/aggregator 176. At step 510, the alternative therapy module 144 or another portion of the service provider module 104 may access the one or more alternative treatment tables. At step 512, the alternative therapy module 144 or another portion of the service provider module 104 may query the one or more alternative treatment tables to determine whether an alternative treatment is available. In one implementation, the query may be based upon the Service Provider ID and the RxNorm and/or product identifier (e.g., NDC) identified in the alternative treatment search request 214. If no alternative treatment is identified, the NO branch is followed to step 514. On the other hand, if an alternative treatment is identified, the YES branch is followed to step 518.

If at step 512 no alternative treatments were identified, at step 514 the service provider computer 104 may transmit a no alternative treatment available message 218 to the healthcare provider device 102 via EHR vendor/aggregator 176. At step 516, the service provider computer 104 may determine whether another alternative treatment search request was received from the healthcare provider 102 via EHR vendor/aggregator 176. If another alternative treatment search request was received, the YES branch is followed and the process may return to step 510. On the other hand, if no other alternative treatment search requests were received, the process then continues to the END step.

If an alternative treatment is identified at step 512, at step 518, the service provider computer 104 may generate a secondary prescription request 220. In one implementation, the secondary prescription request 220 may be formatted in accordance with a version of the National Council for Prescription Drug Programs (NCPDP) Telecommunication Standard, although other standards may be utilized as well as described herein with respect to prescription request 204. The service provider computer 104 electronically transmits the secondary prescription request 220 to the pharmacy claims processor computer 106 in step 520. For example, a secondary prescription request 220 can be electronically transmitted from the service provider computer 104 to the pharmacy claims processor computer 106 via the network 110.

The pharmacy claims processor computer 106 receives and processes the prescription request in step 522 to determine if the patient has coverage, to determine to what extent the patient's coverage covers the requested product or service identified in the request 220, and to generate a secondary prescription response 222 as to whether the request 220 is approved or denied. As described herein with respect to responses 206 and/or 210, the secondary prescription response 222 can include, but are not limited to, accepted, approved, captured, denied (e.g., rejected), and denied (e.g., rejected) with request for additional information and resubmission. In certain exemplary embodiments, the responses can be input into a field of the secondary prescription request 220 that is recognized by the service provider computer 104 and/or the healthcare provider computer 102. Typically, if the response for the request 220 is approved, the secondary prescription response 222 provides the amount of the cost of the medication, product, or service that will be covered by the pharmacy claims processor computer 106 (the total amount paid, which is provided in the Total Amount Paid field of the secondary prescription response 222), any amount applied to a patient deductible which is provided in the amount applied to periodic deductible field of the secondary prescription response 222), the patient pay amount (which is provided in the Patient Pay Amount field of the secondary prescription response 222), a pharmacy name field populated with a short pharmacy name corresponding to the submitted service provider ID on the secondary prescription request 220, and/or a pharmacy street address populated with a pharmacy street address corresponding to the submitted service provider ID on the secondary prescription request 220. On the other hand, if the response is a denial, the secondary prescription response 222 provides the reason for the denial (e.g., in the form of a denial code, for example, patient not covered, Cardholder ID submitted in the request is inactive, prior authorization required, medication not covered, claim limit exceeded, quantity exceeded, days' supply exceeded, etc.).

At step 524, the pharmacy claims processor computer 106 electronically transmits the secondary prescription response 222 to the service provider computer 104 via, for example, the network 110. At step 526, the alternative therapy module 144 or another portion of the service provider computer 104 may determine whether the product in the secondary prescription response 222 was approved by the pharmacy claims processor (e.g., the pharmacy claims processor 106). In one example, the alternative therapy module 144 may identify a status of the secondary prescription response 222 as an approved status or as a denied status. In one example implementation, the status may be identified based upon a status indicator in field in the secondary prescription response 222. If the alternative treatment was denied, the NO branch is followed to step 528. On the other hand, if the alternative treatment was approved, the YES branch is followed to step 530.

If the alternative treatment is denied by the pharmacy claims processor computer 106, at step 526, at step 528 the service provider computer 104 may transmit a denial message to the healthcare provider device 102 via EHR vendor/aggregator 176. In one implementation, a prescription benefit check response 224 may include the denial message, which includes, without limitation, denial information from the secondary prescription response 222. For example, denial information from the secondary prescription response 222 may be inserted into a field (e.g., a text field) of the prescription benefit check response 224. Alternatively, the secondary prescription benefit check response 224 may be appended or otherwise electronically transmitted with the prescription response 222. The process then continues to the END step.

However, if the alternative treatment was approved by the pharmacy claims processor computer 106, the service provider computer 104 may transmit an alternative treatment message to the healthcare provider device 102 via EHR vendor/aggregator 176. In one implementation, a prescription benefit check response 2224 may include the alternative treatment message which includes, without limitation, the NDC, RxNorm, patient pay amount, etc. from the secondary prescription response 222. For example, the alternative treatment information may be inserted into a field (e.g., a text field) of the prescription benefit check response 224. Alternatively, the secondary prescription benefit check response 224 may be appended or otherwise electronically transmitted with the prescription response 222. The process then continues to the END step.

Figure 6:
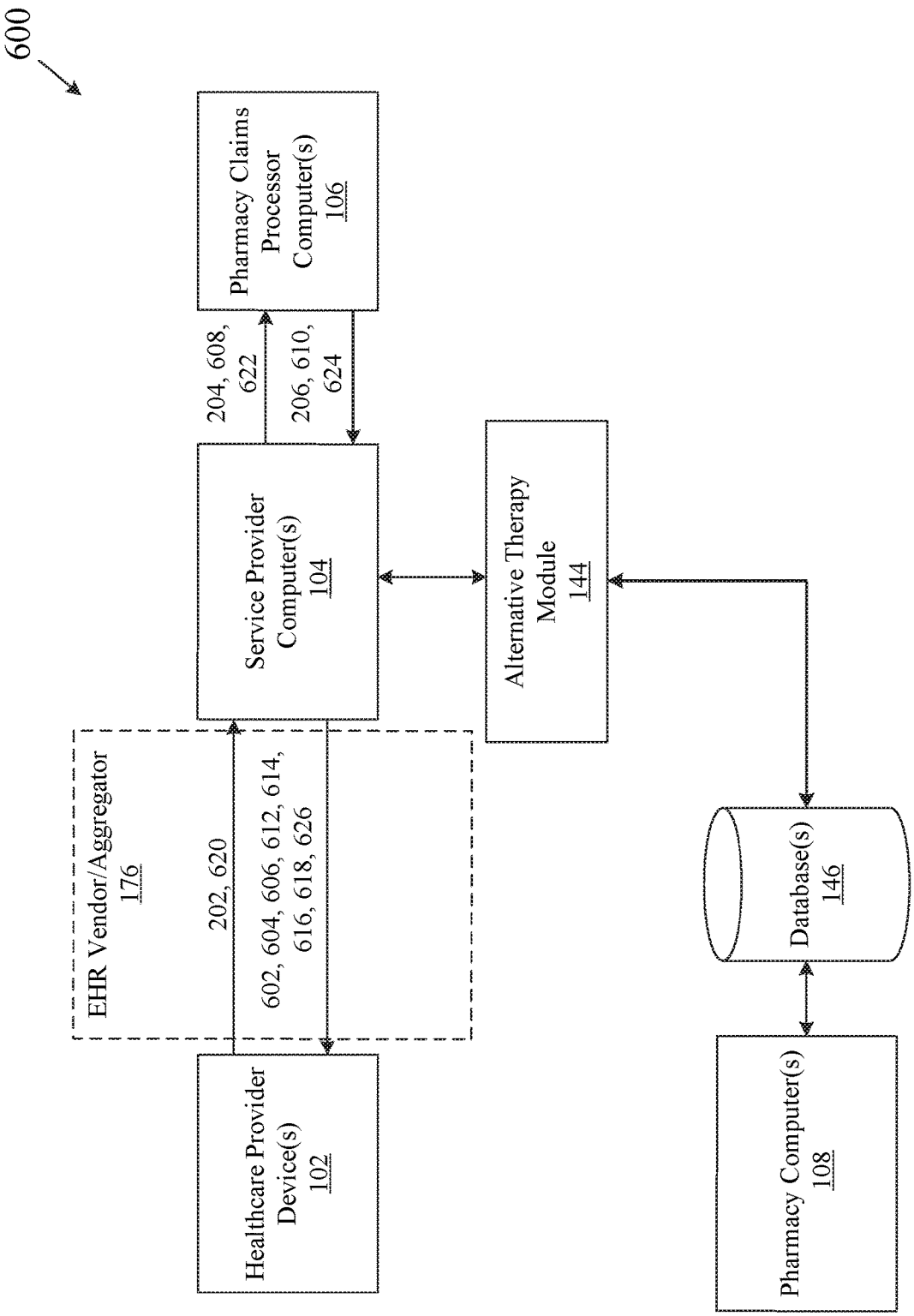
FIG. 6 is a diagram of another example system flow for providing improved alternative therapy identification according to one exemplary embodiment.
Figure 7:
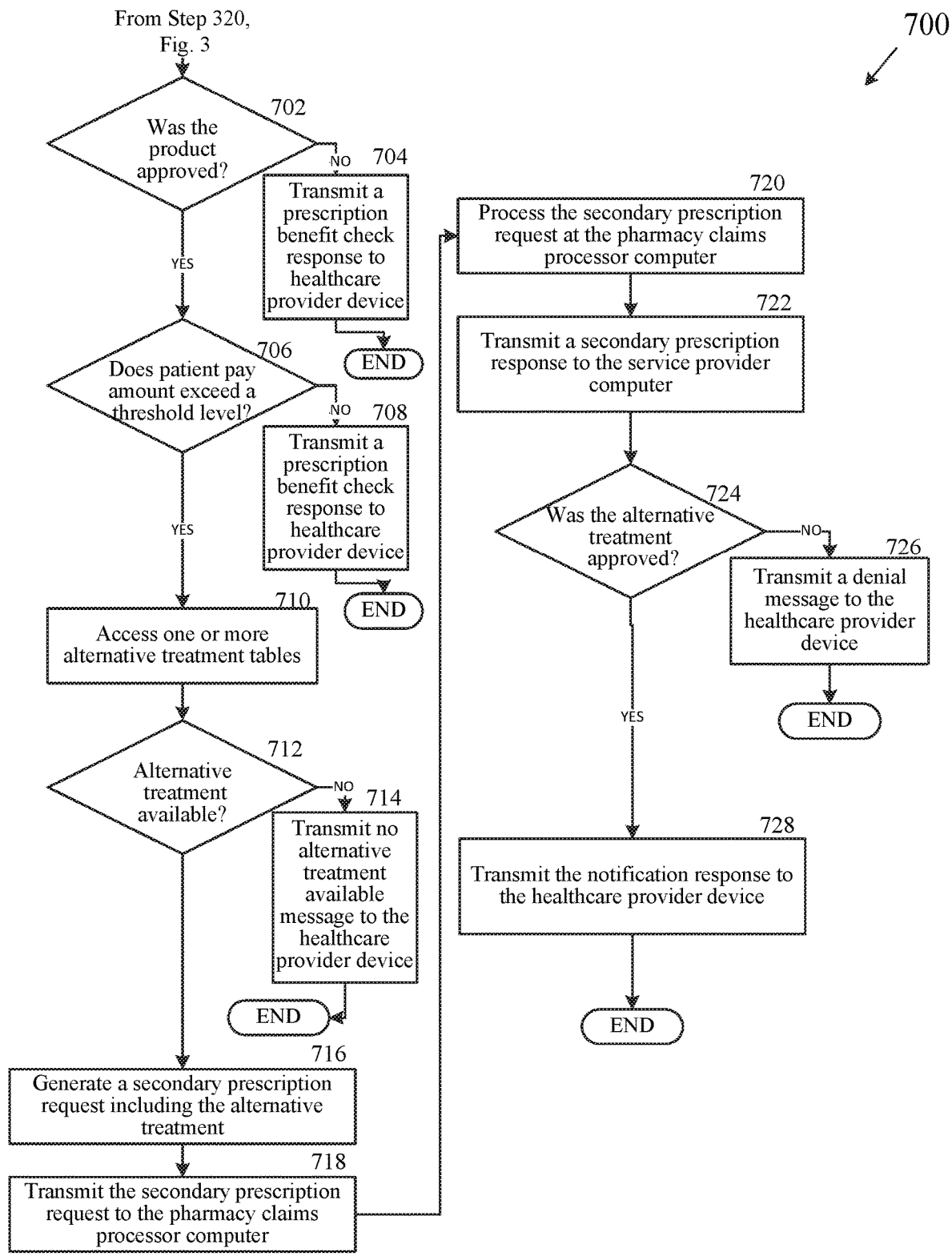
FIG. 7 is another example methodology for providing improved alternative therapy identification according to one exemplary embodiment.

FIG. 6 is a diagram of one example data flow 600 for the improved alternative therapy identification system as part of or in-line with the processing of a prescription request through a service provider, such as through the service provider computer 104 illustrated in FIG. 1. FIG. 7 is a flow chart of an example method 700 for implementing the improved alternative therapy identification system as part of the processing of the prescription request in accordance with one exemplary embodiment. The exemplary method 700, described below, may be performed by a suitable service provider computer 104 and/or alternative therapy module 144.

Referring now to FIGS. 1, 2A, 3, 6, and 7, the exemplary method 700 begins at the START step and proceeds to step 702, where the alternative therapy module 144 or another portion of the service provider computer 104 may determine whether the product in the prescription response 206 was approved by pharmacy claims processor (e.g., the pharmacy claims processor 106). In one example, the alternative therapy module 144 may identify a status of the prescription benefit check response 206 as an approved status or as a denied status. In one example implementation, the status may be identified based upon a status indicator in field in the prescription response 206. If the product identified in the prescription response 206 was denied, the NO branch is followed to step 704. On the other hand, if the product identified in the prescription benefit check response 204 was approved, the YES branch is followed to step 706.

If the product identified in the prescription response was denied, at step 704 a prescription benefit check response 602 may be electronically transmitted by the service provider computer 104 to the healthcare provider device 102 via EHR vendor/aggregator 176. The processing may end after step 704.

If however, the product identified in the prescription response 206 indicates a status of approved, at step 706 the alternative therapy module 144 or another portion of the service provider computer 104 may determine whether the patient pay amount (e.g., patient copay amount) listed in the prescription response 206 exceeds a patient payment threshold level. For example, the prescription response 206 may include a field provides the prescriber the patient pay amount for the product prescribed in the prescription benefit check request 202. The alternative therapy module 144 may compare that patient pay amount to one or more patient payment threshold levels accessed in one or more patient payment threshold tables. In one implementation, a patient payment threshold level may correspond to a dollar amount (e.g. $100, $50, $25, etc.) that a patient pay amount (e.g., a patient copay amount) may not exceed for a particular product prescribed (e.g., a therapeutic classification). The one or more patient payment threshold tables may be organized at a vendor level and may be accessed by the service provider computer via the EHR vendor/aggregator 176, database 146, and/or the data files 138. The vendor may set one or more patient payment threshold levels specific to each RxNorm. For example, the prescription benefit check response 602 may include a patient payment amount of $50 for the prescribed product Lisinopril. The alternative therapy module 144 may access the patient payment threshold table to determine whether the returned patient payment amount returned by the pharmacy claims processor computer 106 exceeds the patient payment threshold for ACE inhibitors, the therapeutic class which Lisinopril belongs. If the patient payment amount does not exceed the patient payment threshold level, the NO branch is followed and processing may continue to step 708. If however, the patient payment amount does exceed the patient payment threshold level, the YES branch is followed and processing may continue to step 710.

If the patient payment threshold level was not exceeded, at step 708 a prescription benefit check response 604 may be electronically transmitted by the service provider computer 104 to the healthcare provider device 102 via EHR vendor/aggregator 176. The processing may end after step 708

If however, the patient payment threshold level was exceeded, at step 710 the alternative therapy module 144 or another portion of the service provider module 104 may access one or more alternative treatment tables. At step 712, the alternative therapy module 144 or another portion of the service provider module 104 may query the one or more alternative treatment tables to determine whether an alternative treatment for the prescribed product may be available. In one implementation, the query may be based upon the Service Provider ID identified in the prescription response 206. In one implementation, the alternative therapy module 144 may search for an alternative treatment table corresponding to the pharmacy name field in the prescription response 206 populated with a short pharmacy name corresponding to the submitted service provider ID on the prescription benefit check request 202. The alternative therapy module 144 may parse the identified alternative treatment table for the RxNorm and/or NDC identified in the prescription response 206 and/or in the corresponding prescription benefit check request 202. Continuing with the Lisinopril example, the alternative therapy module 144 may search for an alternative ACE inhibitor with historical data corresponding to an average cost of a drug (e.g., a usual and customary cost). For example, the alternative therapy module 144 may determine that an alternative ACE inhibitor Benazepril has the lowest average drug cost for the specific pharmacy chain/group identified by the Service Provider ID. If no alternative treatment is identified, the NO branch is followed and processing may continue to step 714. On the other hand, if an alternative treatment is identified, the YES branch is followed and processing may continue to step 716.

If at step 712 no alternative treatments were identified for the prescribed product, the service provider computer 104 may transmit a no alternative treatment available message to the healthcare provider device 102 via EHR vendor/aggregator 176. In one implementation, a prescription benefit check response 606 may include the no alternative treatment available message. For example, the no alternative treatment available message may be inserted into a text field of the prescription benefit check response 606. The process then continues to the END step.

If however, at step 712 an alternative treatment was identified for the prescribed product, the service provider computer 104 may generate a secondary prescription request 608. at step 716 In one implementation, the secondary prescription request 608 may be formatted in accordance with a version of the National Council for Prescription Drug Programs (NCPDP) Telecommunication Standard, although other standards may be utilized as well as described herein with respect to prescription benefit check request 202. The service provider computer 104 electronically transmits the secondary prescription request 608 to the pharmacy claims processor computer 106 in step 718. For example, a secondary prescription request 608 can be electronically transmitted from the service provider computer 104 to the pharmacy claims processor computer 106 via the network 110.

The pharmacy claims processor computer 106 receives and processes the healthcare request in step 720 to determine if the patient has coverage, to determine to what extent the patient's coverage covers the requested product or service identified in the request 608, and to generate a secondary prescription response 610 as to whether the request 608 is approved or rejected. As described herein with respect to prescription responses, the prescription response 610 can include, but are not limited to, accepted, approved, captured, denied (e.g., rejected), and denied (e.g., rejected) with request for additional information and resubmission. In certain exemplary embodiments, the responses can be input into a field of the second prescription request 608 that is recognized by the service provider computer 104 and/or the healthcare provider computer 102. Typically, if the response for the request 608 is approved, the secondary prescription response 610 provides the amount of the cost of the medication, product, or service that will be covered by the pharmacy claims processor 106 (the total amount paid, which is provided in the Total Amount Paid field of the secondary prescription response 610), any amount applied to a patient deductible which is provided in the amount applied to periodic deductible field of the secondary prescription benefit check response 610), the patient pay amount (which is provided in the Patient Pay Amount field of the secondary prescription response 610), a pharmacy name field populated with a short pharmacy name corresponding to the submitted service provider ID on the secondary prescription request 608, and/or a pharmacy street address populated with a pharmacy street address corresponding to the submitted service provider ID on the secondary prescription request 608. On the other hand, if the response is a denial, the secondary prescription response 610 provides the reason for the denial (e.g., in the form of a denial code, for example, patient not covered, Cardholder ID submitted in the request is inactive, prior authorization required, medication not covered, claim limit exceeded, quantity exceeded, days' supply exceeded, etc.).

At step 722, the pharmacy claims processor computer 106 electronically transmits the secondary prescription response 610 to the service provider computer 104 via, for example, the network 110. At step 724, the alternative therapy module 144 or another portion of the service provider computer 104 may determine whether product in the secondary check response 610 was approved by the pharmacy claims processor (e.g., the pharmacy claims processor 106). In one example, the alternative therapy module 144 may identify a status of the secondary prescription response 610 as an approved status or as a denied status. In one example implementation, the status may be identified based upon a status indicator in field in the secondary prescription response 610. If the alternative treatment was denied, the NO branch is followed to step 726. On the other hand, if the alternative treatment was approved, the YES branch is followed to step 728.

If the alternative treatment is denied by the pharmacy claims processor computer 106, at step 726, the service provider computer 104 may transmit a denial message to the healthcare provider device 102 via EHR vendor/aggregator 176. In one implementation, a prescription benefit check response 612 may include the denial message, which includes, without limitation, denial information from the secondary prescription response 610. For example, denial information from the secondary prescription response 610 may be inserted into a field (e.g., a text field) of the prescription benefit check response 612. Alternatively, the secondary prescription benefit check response 612 may be appended or otherwise electronically transmitted with the prescription response 610. The process then continues to the END step.

However, if the alternative treatment was approved by the pharmacy claims processor computer 106, at step 728 the service provider computer 104 may transmit an alternative treatment message to the healthcare provider device 102 via EHR vendor/aggregator 176. In one implementation, a prescription benefit check response 616 may include the alternative treatment message which includes, without limitation, the NDC, RxNorm, patient pay amount, etc. from the secondary prescription response 610. For example, the alternative treatment information may be inserted into a field of the prescription benefit check response 616 (e.g., a text field). Alternatively, the secondary prescription benefit check response 616 may be appended or otherwise electronically transmitted with the prescription response 610. The process then continues to the END step.

While the flow chart described with respect to FIG. 7 illustrates the process ending following the second request/response, it is to be appreciated that subsequent requests/responses may be generated.

Figure 8:
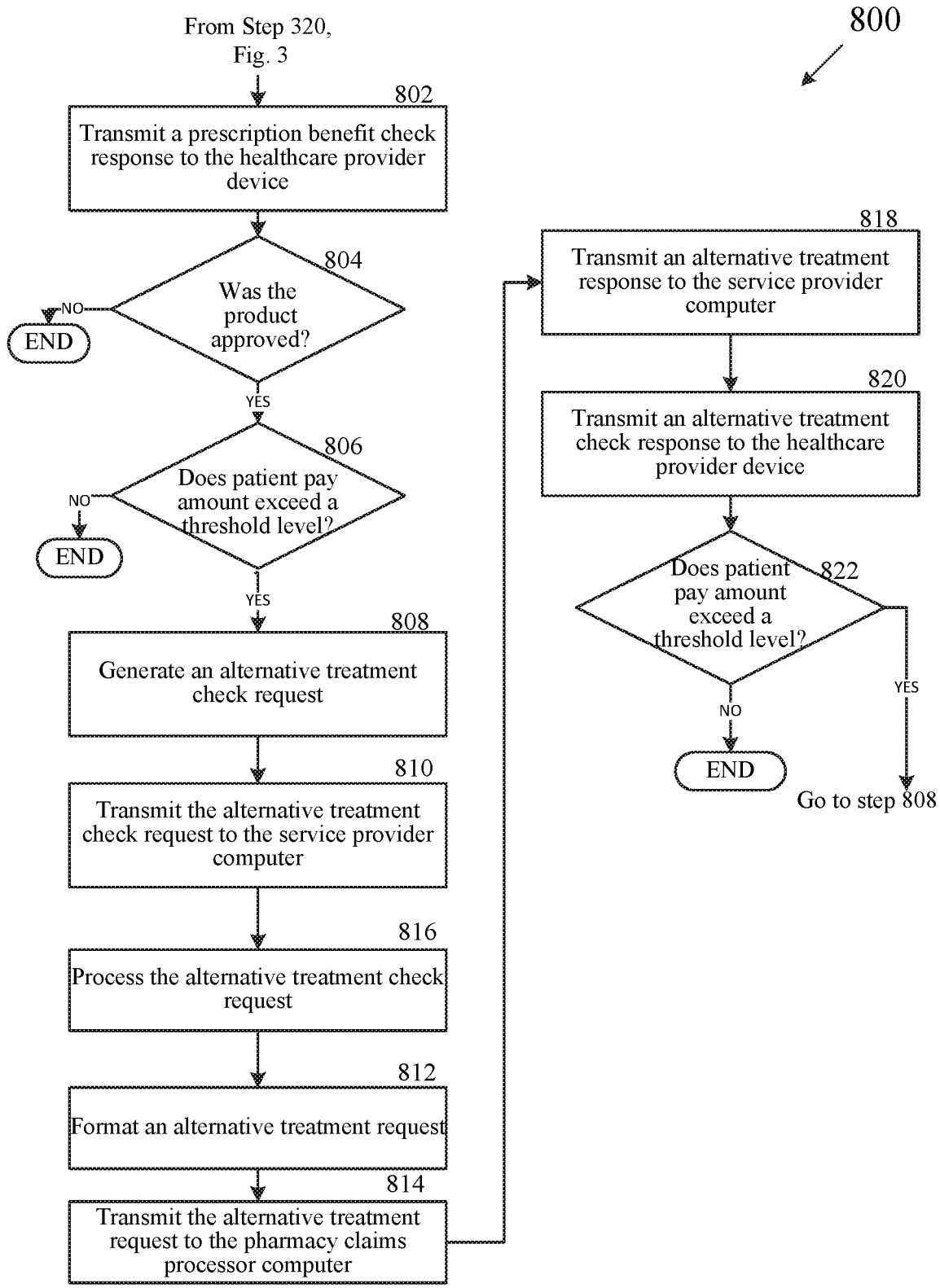
FIG. 8 is another example methodology for providing improved alternative therapy identification according to one exemplary embodiment.

FIG. 8 is a flow chart of an example method 800 for implementing the improved alternative therapy identification system described with reference to FIG. 3 as part of the processing of the prescription request in accordance with one exemplary embodiment. The exemplary method 800, described below, may be performed by a suitable service provider computer 104 and/or alternative therapy module 144.

Referring now to FIGS. 1, 2A, 3, 6, and 8 the exemplary method 800 begins at the START step and proceeds to step 802, where the service provider computer 104 may electronically transmit a prescription benefit check response 618 to the healthcare provider device 102 via an EHR vendor/aggregator 176. In one implementation, the prescription benefit check response 618 includes, without limitation, at least the information included in the prescription response 206 received from the pharmacy claims processor computer 106 (e.g., patient information, patient payment amount, approved/denied status, etc.). At step 804, the healthcare provider device 102 may determine whether the prescription benefit check response includes an approved status indicator or a denied status indicator. If the prescription benefit check response 204 includes a denied status indicator, the NO branch is followed and the process may end after step 804. If on the other hand the prescription benefit check response 618 includes an approved status indicator, the YES branch is followed and the process may continue to step 806.

At step 806, the healthcare provider device 102 may determine whether the patient pay amount identified in the prescription benefit check response 618 exceeds a patient payment threshold level. For example, the prescription benefit check response 618 may include, without limitation, a field that provides the prescriber the patient pay amount for the product prescribed in the prescription benefit check request 202. The healthcare provider device 102 may compare that patient pay amount to one or more patient payment threshold levels accessed in one or more patient payment threshold tables. The one or more patient payment threshold tables may be organized at a vendor level and accessed via the EHR vendor/aggregator 176. The vendor associated with via the EHR vendor/aggregator 176 may set one or more patient payment threshold levels specific to each RxNorm. In one implementation, a patient payment threshold level may correspond to a dollar amount (e.g. $100, $50, $25, etc.) that a patient pay amount (e.g., a patient copay amount) may not exceed for a particular product prescribed (e.g., a therapeutic classification). For example, Each a patient payment threshold levels specific may be established at the vendor level such that when the healthcare provider device 102 receives the prescription benefit check response, the healthcare provider device 102 may compare the returned patient payment amount to a patient payment threshold table corresponding to the therapeutic class for the prescribed product. For example, the prescription benefit check response 204 may include a patient payment amount of $50 for the prescribed product Lisinopril. If the patient payment amount does not exceed the patient payment threshold level, the NO branch is followed and processing may continue to the END step. If however, the patient payment amount does exceed the patient payment threshold level, the YES branch is followed and processing may continue to step 808.

At step 808, the user (e.g., user 126) of the healthcare provider device 102 may generate a request for an alternative treatment check request 620. In one implementation, the alternative treatment check request 620 may include, without limitation, an alternative treatment selected by the prescriber as well as information included in the original prescription benefit check request 202, for example, the patient's pharmacy information (e.g., Service Provider ID, pharmacy name, pharmacy address, etc.) a RxNorm indicating the desired therapeutic class, BIN number, patient identification information, etc.

At step 810, the healthcare provider device 102 electronically transmits the alternative treatment check request 620 to the service provider computer 104. At step 812, the service provider computer 104 may format an alternative treatment request 622, and at step 814, the service provider computer 104 may transmit the alternative treatment request 622 to the pharmacy claims processor computer 106 via network 110. The pharmacy claims processor computer 106 receives and processes the alternative treatment request in step 816 to determine if the patient has coverage, to determine to what extent the patient's coverage covers the requested product or service identified in the request 622, and to generate an alternative treatment response 624 as to whether the request 622 is approved or rejected. As described herein with respect to responses 206, the alternative treatment response 624 can include, but are not limited to, accepted, approved, captured, denied (e.g., rejected), and denied (e.g., rejected) with request for additional information and resubmission. In certain exemplary embodiments, the responses can be input into a field of the alternative treatment request 622 that is recognized by the service provider computer 104 and/or the healthcare provider computer 102. Typically, if the response for the request 622 is approved, the alternative treatment response 624 provides the amount of the cost of the medication, product, or service that will be covered by the pharmacy claims processor computer 106 (the total amount paid, which is provided in the Total Amount Paid field of the alternative treatment response 624), any amount applied to a patient deductible which is provided in the amount applied to periodic deductible field of the alternative treatment response 624), the patient pay amount (which is provided in the Patient Pay Amount field of the alternative treatment response 624), a pharmacy name field populated with a short pharmacy name corresponding to the submitted service provider ID on the alternative treatment request 622, and/or a pharmacy street address populated with a pharmacy street address corresponding to the submitted service provider ID on the alternative treatment request 622. On the other hand, if the response is a denial, the alternative treatment response 624 provides the reason for the denial (e.g., in the form of a denial code, for example, patient not covered, Cardholder ID submitted in the request is inactive, prior authorization required, medication not covered, claim limit exceeded, quantity exceeded, days' supply exceeded, etc.).

At step 818, the pharmacy claims processor computer 106 electronically transmits the alternative treatment response 624 to the service provider computer 104 via, for example, the network 110. At step 820, the service provider 104 transmits an alternative treatment check response 626 to the healthcare provider device 102 via, for example, the network 110 that includes information from the alternative treatment response 624. At step 822, the healthcare provider device 102 may determine whether the patient pay amount identified in the alternative treatment check response 626 exceeds a patient payment threshold level. For example, the patient payment threshold level is $50 for the therapeutic class of ACE inhibitors, as described at step 806. If the patient payment amount does not exceed the patient payment threshold level, the NO branch is followed and processing may continue to the END step. If however, the patient payment amount does exceed the patient payment threshold level, the YES branch is followed and processing may continue to step 808.

Figure 9:
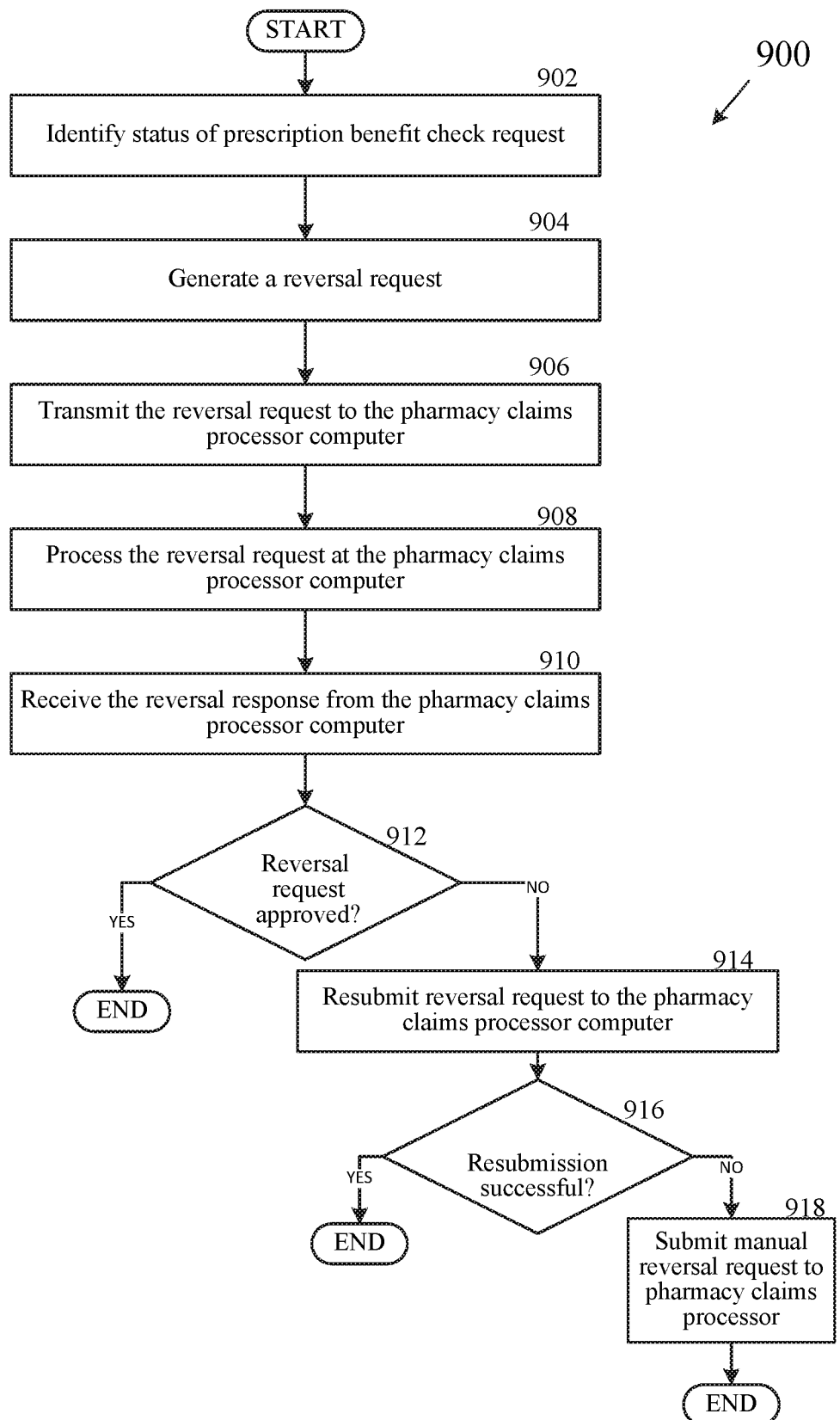
FIG. 9 is an exemplary methodology for providing improved alternative therapy identification according to one exemplary embodiment.

FIG. 9 illustrates an example method 900 for receiving a communicating a reversal request, according to the example embodiment of the disclosure.

Referring now to FIGS. 1A, 2A, and 3-8 the exemplary method 900 begins at the START step and continues to step 902, where the service provider computer 104 may identify where the prescription benefit check request 202 was approved. In one non-limiting example, the service provider computer 104 may determine whether the prescription benefit check 202 was approved by identifying the request status indicator field in the prescription benefit check response 204. If the request status indicator field is populating a "P", then the request was approved. If the request status indicator field is populated with an "R", then the request was denied.

At step 904, the service provider computer 104 may generate a reversal request based at least in part upon the corresponding request type (e.g. B1 or D1) and the corresponding defined NCPDP Telecom format described herein.

At step 906, the service provider computer 104 may electronically transmit the reversal request to the pharmacy claims processor computer 106. In one implementation, the pharmacy claims processor computer 106 is the same benefits computer that the prescription benefit check request 202 was previously submitted to. At step 908, the pharmacy claims processor computer 106 may process the reversal request. At step 910, the service provider computer 104 may receive the reversal request response from the pharmacy claims processor computer 106.

At step 912, the service provider computer 104 may determine whether the reversal request was approved. If the reversal request was approved, the YES branch is followed and the process may end after step 912. If the reversal request was not approved, the NO branch is followed and processing may continue to step 914.

At step 914, the service provider computer 104 may resubmit the reversal request to the pharmacy claims processor computer 106. The reversal request may be resubmitted to the pharmacy claims processor computer 106 for a predetermined number of attempts. At step 916, the service provider computer 104 may determine whether the resubmission of the reversal request was successful. If the resubmission of the reversal request was approved, the YES branch is followed and the process may end after step 916. If the resubmission of the reversal request was not approved, then NO branch is followed and processing may proceed to step 918.

At step 918, the service provider computer 104 may submit a manual reversal request to the pharmacy claims processor computer 106. The method 900 may end after step 918.

The methods described and shown in FIGS. 3, 4, 5, 7, 8, and 9 may be carried out or performed in any suitable order as desired in various embodiments. Additionally, in certain exemplary embodiments, at least a portion of the operations may be carried out in parallel. Furthermore, in certain exemplary embodiments, less than or more than the operations described in FIGS. 3, 4, 5, 7, 8, and 9 may be performed.

Figure 2B:
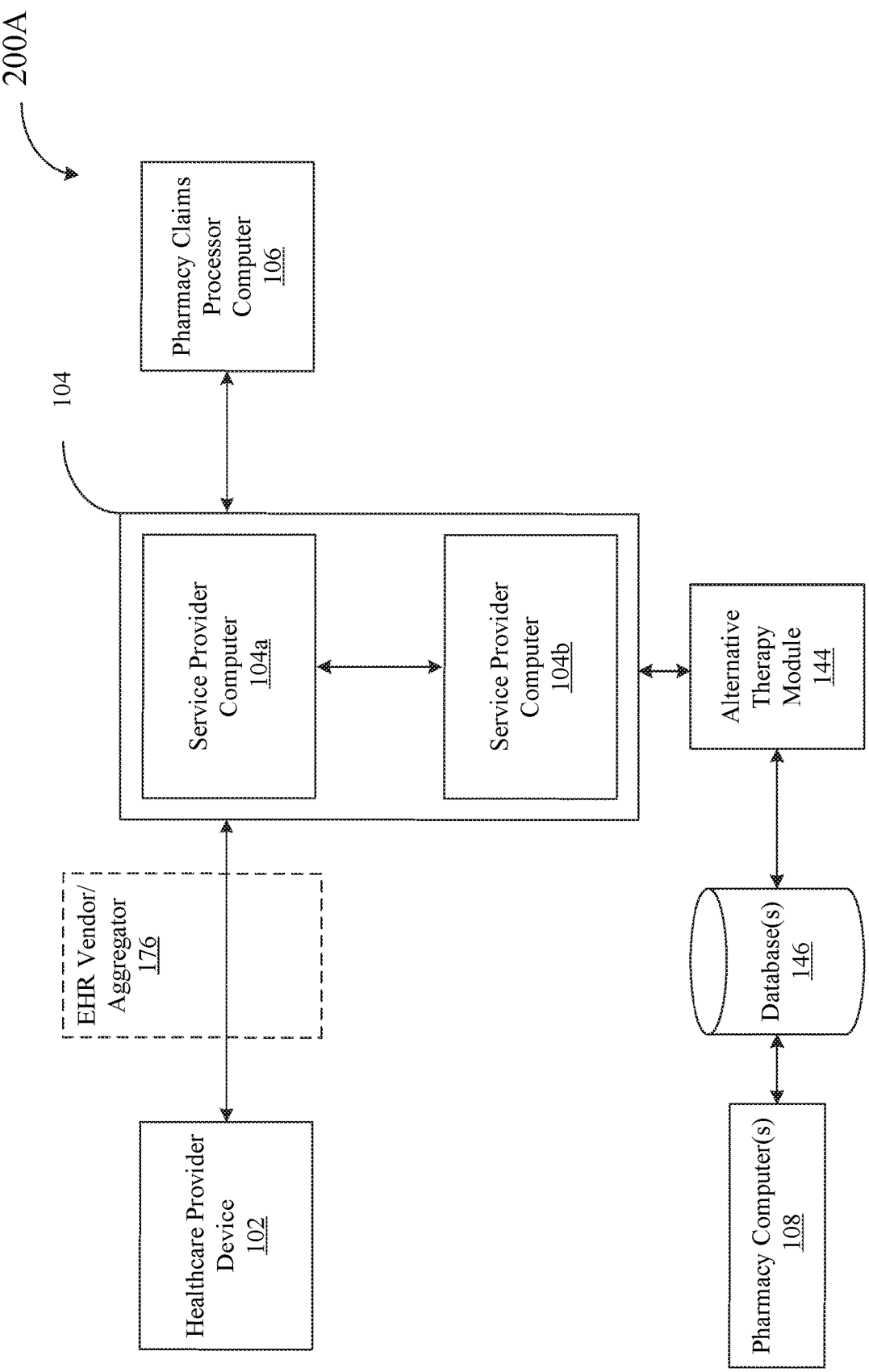
FIG. 2B is a diagram of another example system flow for providing improved alternative therapy identification according to an alternative exemplary embodiment.

Likewise, while FIGS. 3, 4, 5, 7, 8, and 9 have been described primarily in conjunction with FIG. 2A, it will be appreciated that variations of FIG. 2A are available. As shown by the system 200A of FIG. 2B, the service provider computer 104 may include two or more distinct service provider computers 104a and 104b that are in communication with each other. These distinct service provider computers 104a and 104b may be owned, operated, and/or located by the same or distinct and wholly unrelated companies. The service provider computer 104a may be operative with the healthcare provider computer 102, while the service provider computer 104b may be operative with other healthcare provider computers and/or the pharmacy computers. However, the service provider computer 104b may have a data processing arrangement with the service provider computer 104a. Under the data processing arrangement, the service provider computer 104a may be permitted to utilize the adherence monitoring services of the service provider computer 104b, including the operations and use of the alternative therapy module 144 and the data in the database 146 to alternative therapy pricing, as discussed above. Accordingly, the services accessible by the service provider computer 104b, may be available to the healthcare provider computer 102 via the service provider computers 104a and 104b.

While certain example embodiments disclosed herein describe the alternative therapy module 144 as being separate of the service provider computer 104, in alternate embodiments, the alternative therapy module 144 or the functions that it completes may be part of the service provider computer 104. In those embodiments where the alternative therapy module 144 is incorporated into the service provider computer 104, and with regard to the methods described above, the elements describing transmitting or receiving between the service provider computer 104 and the alternative therapy module 144 may be internal transmissions within the service provider computer 104 or may be omitted altogether. Further, while the exemplary embodiments described herein disclose certain steps occurring at the service provider computer 104 and/or the alternative therapy module 144, in alternative embodiments those steps described with reference to FIGS. 1-9 may alternately be completed at a healthcare provider computer 102, a pharmacy claims processor computer 106, an alternative therapy module 144, any combination thereof, and/or a combination of those devices along with the service provider computer 104. In those alternate embodiments, certain transmission/receiving blocks described above with reference to FIGS. 1-9 may be omitted while others may be added, as understood by one or ordinary skill in the art. The intent being that, in alternate embodiments, any of the devices/computers discussed in FIG. 1 are capable of completing all or any part of the methods described with reference to FIGS. 2A-9.

Accordingly, example embodiments disclosed herein can provide the technical effects of creating a system and method that provides real-time or near real time way to facilitate the improved alternative therapy identification system as part of or in-line with the processing of one or more types of prescription requests. In this regard, a patient payment amount corresponding to an alternative treatment may be automatically communicated to a healthcare provider without pharmacy interaction, thus reducing network activity and increasing the efficiency to which alternative therapy pricing information is communicated.

Although example embodiments of the disclosure have been described, one of ordinary skill in the art will recognize that numerous other modifications and alternative embodiments are within the scope of the disclosure. For example, any of the functionality and/or processing capabilities described with respect to a particular device or component may be performed by any other device or component that is properly configured. Furthermore, while various example implementations and architectures have been described in accordance with example embodiments of the disclosure, one of ordinary skill in the art will appreciate that numerous other modifications to the example implementations and architectures described herein are also within the scope of this disclosure.

Certain aspects of the disclosure are described above with reference to block and flow diagrams of systems, methods, apparatuses, and/or computer program products according to example embodiments. It will be understood that one or more blocks of the block diagrams and steps of the flow diagrams, and combinations of blocks in the block diagrams and steps of the flow diagrams, respectively, may be implemented by execution of computer-executable program instructions. Likewise, some blocks of the block diagrams and steps of the flow diagrams may not necessarily need to be performed in the order presented, or may not necessarily need to be performed at all, according to some embodiments. Further, additional components and/or operations beyond those depicted in blocks of the block and/or steps of the flow diagrams may be present in certain embodiments.

Accordingly, blocks of the block diagrams and steps of the flow diagrams support combinations of means for performing the specified functions, combinations of elements or steps for performing the specified functions and program instruction means for performing the specified functions. It will also be understood that each block of the block diagrams and step of the flow diagrams, and combinations of blocks in the block diagrams and steps of the flow diagrams, are implemented by special-purpose, hardware-based computer systems that perform the specified functions, elements or steps, or combinations of special-purpose hardware and computer instructions.

Computer-executable program instructions may be loaded onto a special-purpose computer or other particular machine, a processor, or other programmable data processing apparatus to produce a special-purpose machine, such that execution of the instructions on the computer, processor, or other programmable data processing apparatus causes one or more functions or steps specified in the flow diagrams to be performed. These computer program instructions may also be stored in a computer-readable storage medium (CRSM) that upon execution may direct a computer or other programmable data processing apparatus to function in a particular manner, such that the instructions stored in the computer-readable storage medium produce an article of manufacture including instruction means that implement one or more functions or steps specified in the flow diagrams. The computer program instructions may also be loaded onto a computer or other programmable data processing apparatus to cause a series of operational elements or steps to be performed on the computer or other programmable apparatus to produce a computer-implemented process.

Additional types of CRSM that may be present in any of the devices described herein may include, but are not limited to, programmable random access memory (PRAM), SRAM, DRAM, RAM, ROM, electrically erasable programmable read-only memory (EEPROM), flash memory or other memory technology, compact disc read-only memory (CD-ROM), digital versatile disc (DVD) or other optical storage, magnetic cassettes, magnetic tape, magnetic disk storage or other magnetic storage devices, or any other medium which can be used to store the information and which can be accessed. Combinations of any of the above are also included within the scope of CRSM. Alternatively, computer-readable communication media (CRCM) may include computer-readable instructions, program modules, or other data transmitted within a data signal, such as a carrier wave, or other transmission. However, as used herein, CRSM does not include CRCM.

Although example embodiments have been described in language specific to structural features and/or methodological acts, it is to be understood that the disclosure is not necessarily limited to the specific features or acts described. Rather, the specific features and acts are disclosed as illustrative forms of implementing the example embodiments. Conditional language, such as, among others, "can," "could," "might," or "may," unless specifically stated otherwise, or otherwise understood within the context as used, is generally intended to convey that certain example embodiments could include, while other example embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

What is claimed is:

1. A system for alternative therapy identification, comprising;

at least one memory operable to store computer-executable instructions and a data file storing a routing table identifying a destination of communications received from a pharmacy claims processor computer;

a database or data file storing one or more alternative therapy tables configured in a first predefined format, and comprising a therapeutic class, one or more product identifiers, and a product cost corresponding to each product identifier; and at least one processor configured to access the at least one memory and execute the computer-executable instructions to:

receive a prescription benefit request configured in a different predefined format, and comprising at least one or more patient data, one or more patient pharmacy benefit data, an identifier for a prescribed medication, and one or more prescriber data;

parse the prescription benefit request to generate a prescription identifier in a standardized format that is compatible with the first predefined format of the alternative therapy tables;

in real-time or near real time:
access pharmacy data stored in the one or more alternative therapy tables stored in the database or data file;
automatically search the one or more alternative therapy tables based upon the prescribed medication;
identify, based at least upon the identifier for the prescribed medication and the product cost for one or more product identifiers of the same therapeutic class as the prescribed medication in the one or more alternative therapy tables, an alternative product equivalent to the prescribed medication; automatically generate a second prescription benefit request, configured in the different predefined format in which the prescription benefit request was received, such that the second prescription benefit request is compatible with the pharmacy claims processor computer, wherein generating the second prescription benefit request comprises generating a benefit request based upon the prescribed medication and generating a benefit request based upon the identified alternative product equivalent to the prescribed medication that is identified by the one or more alternative therapy tables, wherein the benefit request based upon the prescribed medication comprises at least the one or more patient data, the one or more patient pharmacy benefit data, and the prescription identifier of the prescribed medication and the benefit request based upon the identified alternative product comprises information from the one or more alternative therapy tables including an identifier for the identified alternative product;

receive, from the pharmacy claims processor computer in response to transmission of the benefit request to the pharmacy claims processor computer based upon the prescribed medication and the benefit request based upon the identified alternative product, a prescription response and an alternative therapy response, wherein the prescription response comprises at least a patient pay amount for the prescribed medication and a response status indicating a denial or approval of the prescribed medication, and wherein the alternative therapy response comprises at least an approved status or a denied status and an alternative therapy patient pay amount for the identified alternative product; and without pharmacy or patient interaction, automatically transmit a prescription benefit response based upon the routing table, wherein the prescription benefit response comprises the prescription response including at least the patient pay amount for the prescribed medication and the alternative therapy response including at least the patient pay amount for the alternative product.

2. The system of claim 1, further comprising one or more patient payment threshold levels, the one or more payment threshold levels corresponding to a dollar amount that a patient pay amount may not exceed for a particular prescribed medication, wherein the one or more patient payment threshold tables are based on pharmacy data comprising request or response data previously submitted or received by a pharmacy computer.

3. The system of claim 1, wherein the denied status for the prescribed medication is based at least upon detection of a response field comprising a field status indicator indicating that the request was denied.

4. The system of claim 1, wherein the processor is further configured to access the at least one memory and execute the computer-executable instructions to:
receive the second prescription benefit request for the alternative product equivalent to the prescribed medication.

5. The system of claim 1, wherein the alternative therapy response further comprises the status of the alternative product and a product identifier for the alternative product.

6. The system of claim 1, wherein the alternative product is determined to be equivalent to the prescribed medication where the alternative product and the prescribed medication are from a same therapeutic class.

7. The system of claim 1, wherein the processor is further configured to access the at least one memory and execute the computer-executable instructions to:
where the alternative therapy response includes at least a response field comprising a field status indicator indicating that the request was approved,
direct the communication of a reversal request for the alternative product to the pharmacy claims processor computer, wherein the reversal request comprises at least the data from the prescription benefit request comprising at least the patient data, and the patient pharmacy benefit data from the prescription benefit request.

8. The system of claim 1, wherein the data from the alternative therapy response is inserted into the prescription benefit response or the alternative therapy response is appended to the prescription response prior to transmission.

9. A computer-implemented method for alternative therapy identification, comprising:
receiving, by a service provider computer associated with a service provider and comprising one or more computer processors, a prescription benefit request comprising at least one or more patient data, one or more patient pharmacy benefit data, an identifier for a prescribed medication, and one or more prescriber data;
in real-time or near real time:
accessing pharmacy data stored in one or more alternative therapy tables configured in a first predefined format, different from a different predefined format of the prescription benefit request, wherein the one or more alternative therapy tables are stored in a database or data file and comprise a therapeutic class, one or more product identifiers, and a product cost corresponding to each product identifier;
parsing the prescription benefit request to generate a prescription identifier in a standardized format that is compatible with the first predefined format of the alternative therapy tables, and automatically searching the one or more alternative therapy tables based upon the prescribed medication;
identifying, by the service provider computer and based at least upon the identifier for the prescribed medication and the product cost for one or more product identifiers of the same therapeutic class as the prescribed medication in the one or more alternative therapy tables, an alternative product equivalent to the prescribed medication;
automatically generating, by the service provider computer, a second prescription benefit request, configured in the different predefined format in which the prescription benefit request was received, such that the second prescription benefit request is compatible with the pharmacy claims processor computer, wherein generating the second prescription benefit request comprises generating a benefit request based upon the prescribed medication and generating a benefit request based upon the identified alternative product equivalent to the prescribed medication that is identified by the one or more alternative therapy tables, wherein the benefit request based upon the prescribed medication comprises at least the one or more patient data, the one or more patient pharmacy benefit data, and the prescription identifier of the prescribed medication and the benefit request based upon the identified alternative product comprises information from the one or more alternative therapy tables including an identifier for the identified alternative product;

receiving, by the service provider computer from the pharmacy claims processor computer in response to transmission of the benefit request to the pharmacy claims processor computer based upon-the prescribed medication and the benefit request based upon the identified alternative product, a prescription response and an alternative therapy response, wherein the prescription response comprises at least a patient pay amount for the prescribed medication and a response status indicating a denial or approval of the prescribed medication, and wherein the alternative therapy response comprises at least an approved status or a denied status and an alternative therapy patient pay amount for the identified alternative product; and without pharmacy or patient interaction, automatically transmitting, by the service provider computer, a prescription benefit response to the healthcare provider computer identified by a routing table, wherein the routing table is stored in a data file and identifies a destination of communications received from a healthcare provider device or the pharmacy claims processor computer, and wherein the prescription benefit response comprises the prescription response including at least the patient pay amount for the prescribed medication and the alternative therapy response including at least the patient pay amount for the alternative product.

10. The computer-implemented method of claim 9, further comprising accessing a patient payment threshold level from one or more patient payment threshold tables, the patient payment threshold level corresponding to a dollar amount that the patient pay amount may not exceed for a particular prescribed medication, wherein the one or more patient payment threshold tables are based on pharmacy data comprising request and response data previously submitted or received by a pharmacy computer.

11. The computer-implemented method of claim 9, wherein the denied status for the prescribed medication is based at least upon the detection of a response field comprising a field status indicator indicating that the request was denied.

12. The computer-implemented method of claim 9 further comprising:

receiving, by the service provider computer, from the healthcare provider device via the EHR vendor/aggregator, the second prescription benefit request for the alternative therapy patient pay amount for the alternative product equivalent to the prescribed medication.

13. The computer-implemented method of claim 9, wherein the alternative therapy response further comprises the status of the alternative product and a product identifier for the alternative product.

14. The computer-implemented method of claim 9, wherein the alternative product is determined to be equivalent to the prescribed medication where the alternative product and the prescribed medication are from a same therapeutic class.

15. The computer-implemented method of claim 9 further comprising:

where the alternative therapy response includes at least a response field comprising a field status indicator indicating that the request was approved, transmitting, by the service provider computer, a reversal request for the alternative product to the pharmacy claims processor computer, wherein the reversal request comprises at least the data from the prescription benefit request comprising at least the patient data, the patient pharmacy benefit data, and the prescriber data from the prescription benefit request.

16. The computer-implemented method of claim 9, wherein the data from the alternative therapy response is inserted into a field of the prescription benefit response or the alternative therapy response is appended to the prescription response prior to the communication to the healthcare provider.

17. The computer-implemented method of claim 9, further comprising:

identifying an instance in which the prescription benefit request was approved; and generating, based on a type of the prescription benefit request, a reversal request for transmission from the service provider computer to the pharmacy claims processor computer.

18. The system of claim 1, wherein the at least one processor is further configured to access the at least one memory and execute the computer-executable instructions to identify an instance in which the prescription benefit request was approved and to generate, based on a type of the prescription benefit request, a reversal request for transmission from a service provider computer to the pharmacy claims processor computer.

\* \* \* \* \*

UNITED STATES PATENT AND TRADEMARK OFFICE
CERTIFICATE OF CORRECTION

| | |
|---|---|
| PATENT NO. | : 11,514,137 B1 |
| APPLICATION NO. | : 15/085166 |
| DATED | : November 29, 2022 |
| INVENTOR(S) | : Kaye et al. |

It is certified that error appears in the above-identified patent and that said Letters Patent is hereby corrected as shown below:

In the Claims

Column 31,
Line 28, "upon-the" should read --upon the--.

Column 33,
Line 9, "upon-the" should read --upon the--.

Signed and Sealed this
Seventeenth Day of October, 2023

Katherine Kelly Vidal
*Director of the United States Patent and Trademark Office*